US012636399B2

(12) United States Patent　　(10) Patent No.:　US 12,636,399 B2
Slotkin et al.　　(45) Date of Patent:　May 26, 2026

(54) PROACTIVE AIR/SURFACE DECONTAMINATION SYSTEM AND DEVICES FOR BUILDING HVAC DUCTS

(71) Applicant: Radical Clean Solutions Ltd., Long Beach, NY (US)

(72) Inventors: Roger Slotkin, Long Beach, NY (US); Ralph T. Kubitzki, Plantation, FL (US)

(73) Assignee: Radical Clean Solutions Ltd., Long Beach, NY (US)

( * ) Notice: Subject to any disclaimer, the term of this patent is extended or adjusted under 35 U.S.C. 154(b) by 601 days.

(21) Appl. No.: 18/075,681

(22) Filed: Dec. 6, 2022

(65) Prior Publication Data

US 2023/0201412 A1　　Jun. 29, 2023

Related U.S. Application Data

(63) Continuation-in-part of application No. 17/861,181, filed on Jul. 9, 2022, and a continuation-in-part of (Continued)

(51) Int. Cl.
　*A61L 9/20*　　　(2006.01)
　*A61L 2/10*　　　(2006.01)

(52) U.S. Cl.
　CPC .................. *A61L 9/205* (2013.01); *A61L 2/10* (2013.01); *A61L 2209/12* (2013.01); *A61L 2209/15* (2013.01); *A61L 2209/16* (2013.01)

(58) Field of Classification Search
　CPC ........ A61L 2/10; A61L 9/20; A61L 2209/111; A61L 2209/12; A61L 2209/15; A61L 2209/20
　See application file for complete search history.

(56) References Cited

U.S. PATENT DOCUMENTS 2,945,554 A　　7/1960　Berly
6,497,840 B1　　12/2002　Palestro et al.
(Continued)

FOREIGN PATENT DOCUMENTS

JP　　　　2010080195 A　　4/2010
WO　PCT/US2022/051886 A　　5/2023

OTHER PUBLICATIONS

LSE (Light Spectrum Enterprises); "Shop UV Lighting-GPH457T5L/4P Ultraviolet UV Lamp Bulb 4-pin Base 18" GPH457T5"; 1300 Industrial Blvd.—Ste B3, Southampton, PA 18966.

(Continued)

*Primary Examiner* — Timothy C Cleveland
(74) *Attorney, Agent, or Firm* — Alfred M. Walker; Thomas A. O'Rourke; James Bongiorno

(57)　　　　　ABSTRACT

A system for decontaminating/neutralizing breathable air and surfaces in an occupied enclosed space, i.e., hydroponic greenhouses, aircraft, rail and road vehicles, in building ducts, or rooms, includes mounting an atmospheric hydroxyl radical generator along an inside surface of an occupied space having respective air inlets and air outlets. The hydroxyl radical generator includes a polygonal housing supporting a plurality of spaced crystal-spliced UV optics medical grade pure quartz, which emit/irradiate ultraviolet in the nanometer wavelength/ultraviolet spectrum of between 100 and 400 nanometers for deactivating and neutralizing atmospheric chemicals and pathogens in breathable air and surfaces. The hydroxyl radicals contact the walls of the reaction chamber housing. The hydroxyl radicals become created and excited to react quickly with impurities including VOC, virus, bacteria and fungi, rendering them inactivated and neutral. The breathable air passes through the polygonal housing and is decontaminated and neutral- (Continued)

ized of impurities before entering the occupied enclosed space.

11 Claims, 18 Drawing Sheets

Related U.S. Application Data application No. 17/826,555, filed on May 27, 2022, and a continuation-in-part of application No. 17/713,959, filed on Apr. 5, 2022, now Pat. No. 12,246,116, which is a continuation-in-part of application No. 17/674,763, filed on Feb. 17, 2022, now Pat. No. 12,390,547, said application No. 17/826,555 is a continuation-in-part of application No. 17/590,270, filed on Feb. 1, 2022, now abandoned, which is a continuation-in-part of application No. 17/545,919, filed on Dec. 8, 2021, said application No. 17/861,181 is a continuation-in-part of application No. 17/545,919, filed on Dec. 8, 2021, said application No. 17/674,763 is a continuation-in-part of application No. 17/545,919, filed on Dec. 8, 2021.

(56) References Cited

U.S. PATENT DOCUMENTS

| | | | |
|---|---|---|---|
| 6,613,277 | B1 | 9/2003 | Monagan |
| 6,805,733 | B2 | 10/2004 | Engel et al. |
| 7,837,933 | B2 | 11/2010 | Sevack et al. |
| 7,976,195 | B2 | 7/2011 | Engel et al. |
| 7,988,923 | B2 | 8/2011 | Fink et al. |
| 8,226,899 | B2 * | 7/2012 | Woodbridge ............. A61L 9/20 |
| | | | 422/186.04 |
| 8,252,099 | B2 | 8/2012 | Worrilow |
| 8,252,100 | B2 | 8/2012 | Worrilow |
| 8,545,753 | B2 | 10/2013 | Sevack et al. |
| 8,747,753 | B2 | 6/2014 | Engel et al. |
| 9,168,323 | B2 | 10/2015 | Morneault |
| 9,522,210 | B2 | 12/2016 | Worrilow |
| 9,675,725 | B2 | 6/2017 | Worrilow |
| 9,884,135 | B2 | 2/2018 | Bystrzynski et al. |
| 9,956,306 | B2 | 5/2018 | Brais et al. |
| 9,980,748 | B2 | 5/2018 | Worrilow |
| 10,857,249 | B2 | 12/2020 | Brais et al. |
| 11,103,611 | B2 | 8/2021 | Elde et al. |
| 2008/0073565 | A1 | 3/2008 | Jeon |
| 2008/0279733 | A1 * | 11/2008 | Glazman ................. F24F 8/192 |
| | | | 422/243 |
| 2015/0114822 | A1 | 4/2015 | Greco |
| 2017/0225973 | A1 | 8/2017 | Henderson et al. |
| 2020/0084983 | A1 | 3/2020 | Liang et al. |
| 2020/0129972 | A1 | 4/2020 | Ozaki et al. |
| 2022/0074615 | A1 * | 3/2022 | Richardson ............... F24F 8/22 |
| 2022/0176005 | A1 * | 6/2022 | Riesenberger ............ A61L 9/20 |

OTHER PUBLICATIONS

Hao Chen, et al.; "A Hydroxyl radical detection system using gas expansion and fast gating laser-induced fluorescence techniques"; The Research Center for Eco-Environmental Sciences, Chinese Academy of Sciences; Journal of Environmental Sciences 65 (2018) 190-200; published by Elsevier B.V.; http//dx.doi.org/10.1016/i.jes. 2017.03.012.

* cited by examiner

Fig. 5A

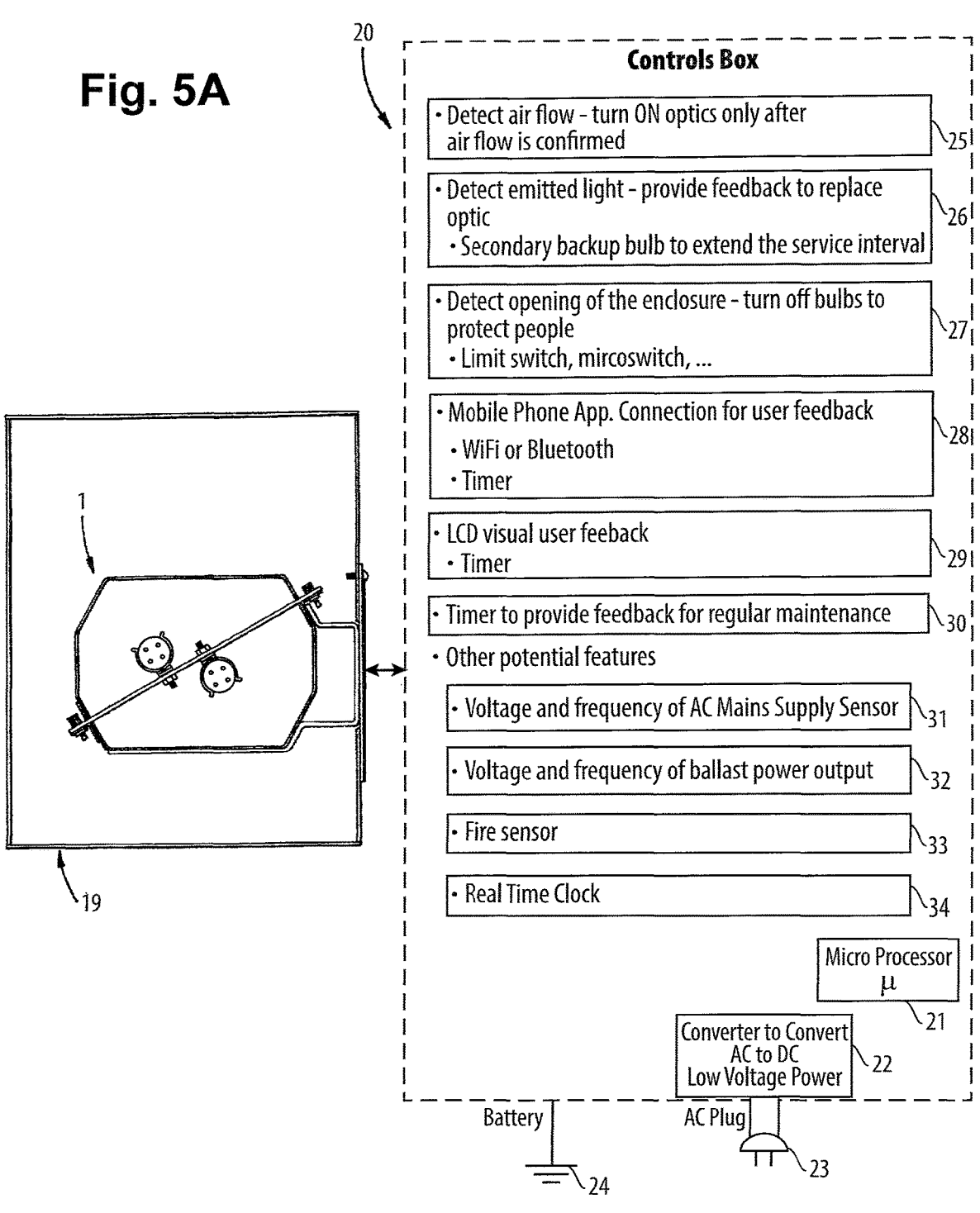

Controls Box

- Detect air flow – turn ON optics only after air flow is confirmed ⟍25

- Detect emitted light – provide feedback to replace optic
  - Secondary backup bulb to extend the service interval ⟍26

- Detect opening of the enclosure – turn off bulbs to protect people
  - Limit switch, mircoswitch, ... ⟍27

- Mobile Phone App. Connection for user feedback
  - WiFi or Bluetooth
  - Timer ⟍28

- LCD visual user feeback
  - Timer ⟍29

- Timer to provide feedback for regular maintenance ⟍30

- Other potential features

- Voltage and frequency of AC Mains Supply Sensor ⟍31

- Voltage and frequency of ballast power output ⟍32

- Fire sensor ⟍33

- Real Time Clock ⟍34

Micro Processor μ ⟍21

Converter to Convert AC to DC Low Voltage Power ⟍22

Battery

AC Plug

⟍24

⟍23

(HVAC Unit Block Diagram)

(Consumer Unit Block Diagram)

ESP32_AP

WiFiManager

Configure WiFi

Info

Exit

No AP set

SSID

Password

Save

Refresh

No AP set

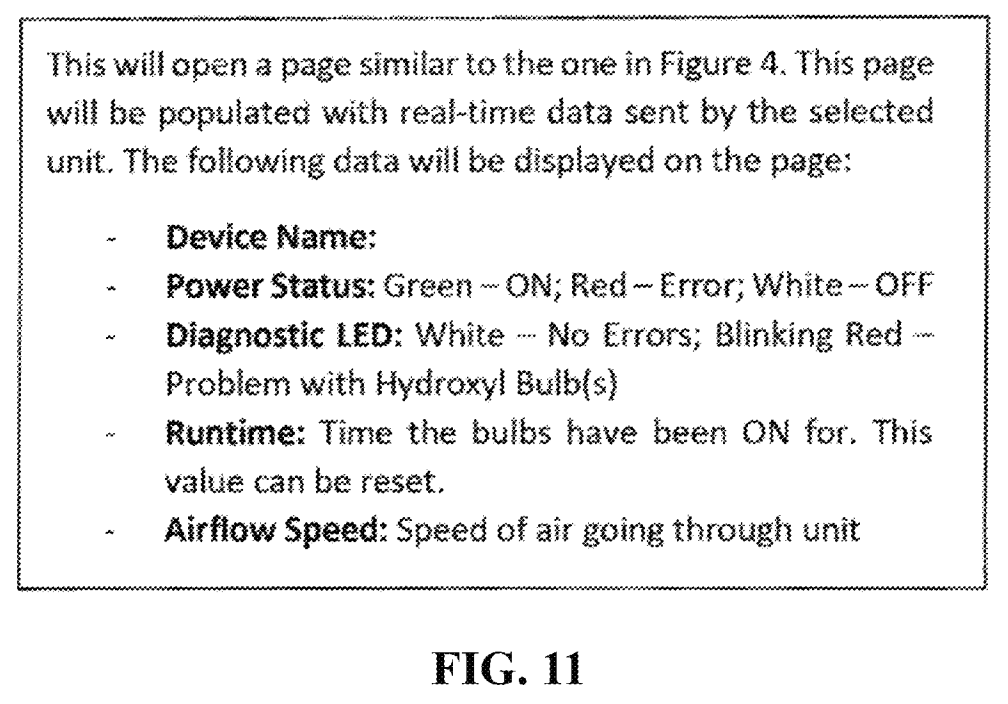

This will open a page similar to the one in Figure 4. This page will be populated with real-time data sent by the selected unit. The following data will be displayed on the page:

- Device Name:
- Power Status: Green — ON; Red — Error; White — OFF
- Diagnostic LED: White — No Errors; Blinking Red — Problem with Hydroxyl Bulb(s)
- Runtime: Time the bulbs have been ON for. This value can be reset.
- Airflow Speed: Speed of air going through unit

FIG. 11

Current Device: HVAC Unit #1

Power Status

Diagnostic LED

Hydroxyl Generation Status

*Run Time*
*24 hours 6 minutes 3 seconds*

Reset Runtime

Airflow Speed 0.687472527
m/s

Reset Runtime

PROACTIVE AIR/SURFACE DECONTAMINATION SYSTEM AND DEVICES FOR BUILDING HVAC DUCTS

RELATED APPLICATIONS

This application is a continuation-in-part (CIP) of application Ser. No. 17/861,181 filed Jul. 9, 2022, which '181 application is a continuation-in-part (CIP) of application Ser. No. 17/545,919 filed Dec. 8, 2021. This application is also a continuation-in part (CIP) of application Ser. No. 17/713, 959 filed Apr. 5, 2022, which '959 application is a continuation-in-part (CIP) of application Ser. No. 17/674,763 filed Feb. 17, 2022, which '763 application is a continuation-in-part (CIP) of application Ser. No. 17/545,919 filed Dec. 8, 2021. This application is also a continuation-in-part (CIP) of application Ser. No. 17/826,555 filed May 27, 2022, which '555 application is a continuation-in-part (CIP) of application Ser. No. 17/590,270, filed Feb. 1, 2022, which '270 application is a continuation-in-part (CIP) of application Ser. No. 17/545,919 filed on Dec. 8, 2021. The '919, '270, '763, '959, '555 and '181 are each incorporated by reference herein. Applicant claims priority under 35 USC § 120 from the 919, '270, '763, '959, '555 and '181 applications.

FIELD OF THE INVENTION

The present invention relates use of a harmonic biomimicry nonchemical photonic process that results in the export of desired atmospheric hydroxyls at precisely the same rate as nature provides (2.6 million per cubic Centimeter—NASA), to neutralize toxic chemicals and pathogens in breathable air/surfaces in stationary or moving human occupied spaces.

BACKGROUND OF THE INVENTION

Ultraviolet light (UV) delivery in the form of directing ultraviolet light on unsanitary surfaces as germicides, bactericides and viricides are disadvantageous because, upon exposure to breathable air in mass transit rail and road vehicles, as well as aircraft and related airborne vehicles, such as helicopters, seating fabrics in building interior ducts and wall surfaces and other human occupied spaces, the ultraviolet light compromises fabrics and doesn't penetrate into crevices between, or in, passenger seats or flight deck seats, located in the flight deck, separately sealed away from the air of the passenger cabin, or in seating fabrics in mass transit rail and road vehicles, in building interior ducts and wall surfaces, in hydroponic greenhouses, in portable room-sized units and other human occupied spaces. Delivery of ultraviolet light for sanitation is limited because the ultraviolet light is only as effective as the actual line of sight of the ultraviolet waves.

DESCRIPTION OF THE PRIOR ART

Methods of Producing Atmospheric Hydroxyls

In the field of physics there are, to date, only a few processes in a device that generates an atmospheric hydroxyl that purportedly are useful in removing contaminants from breathable air. In theory the NASA device produces the hydroxyl in a photo catalytic oxidation (PCO) process, by emitting an ultraviolet irradiation of 254 nanometers as it interfaces with titanium dioxide ($TiO_2$) plating. In theory, the hydroxyl is produced only at the interface site of contact at the surface of the $TiO_2$. The hydroxyl does not exit the airstream and does not have any downstream interaction. Minimal air flow must be maintained at approximately 120 cfm. Typical HVAC systems utilize faster air movement at approximately 2000 cfm and this would not allow for the theoretical hydroxyl to form.

OBJECTS AND SUMMARY OF THE INVENTION

This Summary is provided to introduce a selection of concepts in a simplified form that are further described below in the Detailed Description of the Drawings. This Summary is not intended to identify key features or essential features of the claimed subject matter, nor is it intended to be used to limit the scope of the claimed subject matter.

In contrast, the present invention uses airborne hydroxyl radical molecules, which are of very small molar size and can occupy almost any given space. They can occupy dark crevices that ultraviolet line of sight cannot get access to. The present invention allows for a "Harmonic" of photonic UV frequencies to be applied within a hydroxyl producing reaction chamber. The feed stock is ambient water vapor in air which will have relative humidity, this humidity is the feed stock for the reaction chamber to produce the atmospheric hydroxyl.

This action is called "Bio-Mimicry". The present invention process is a totally green, environmentally friendly nonchemical process that results in the export of the desired atmospheric hydroxyl at precisely the same rate as nature provides, namely, at 2.6 million per cubic centimeter. The atmospheric hydroxyl process begins by exposing ambient water vapor to special UV optics having hydroxyl activation portions made of medical grade pure quartz material. The optics are designed to emit/irradiate Ultraviolet irradiation in the nanometer wavelength/Ultraviolet spectrum of between 100 and 400 nanometers, thereby producing the hydroxyls at the aforementioned quantity of 2.6 million hydroxyls per cubic centimeter, as provided in nature. This is a novel improvement over prior art NASA PCO based technology.

Hydroxyl are groups having the radical "—OH" and are represented by the symbol —OH or HO—, which can have a negative charge or be neutral. The hydroxyl functional group includes one hydrogen atom which is covalently bonded to one oxygen atom. Hydroxyl radicals are very reactive, which react quickly to hydrocarbons, carbon monoxide molecules and other air impurities, such as volatile organic compounds, (VOC), virus, bacteria and fungi.

Many closed HVAC air systems can harbor microscopic bacteria, virus (i.e., Covid-19) and fungi.

For example, aircraft and other airborne transportation vehicles, such as helicopters, seat fabrics on mass transit rail and road vehicles, in building ducts and wall surfaces, in hydroponic greenhouses, and other human occupied spaces, can harbor bacteria and virus in the separate, circulated air systems.

Also, residential rooms in dwellings or assisted living communities can harbor bacteria and virus in the separate, circulated air systems.

Therefore, the present invention is a unique and novel application method for the delivery of safe and natural hydroxyl radicals into breathable air volume containers such as agricultural hydroponic greenhouses and the agricultural plant contents therein, airline flight deck or passenger cabins, and the contents therein, seat fabrics on mass transit rail and road vehicles, in building HVAC ducts and the breathable ambient or heated or cooled air flow contents therein. To be considered as well are upholstered chair seats, benches, contact surfaces such as grab bars, handles in building wall surfaces and other human occupied spaces.

In the present invention, the atmospheric hydroxyl radicals are generated in closed multi-sided housing, preferably polygonal, having therein two or more parallel UV optics which are multi segmented with crystal, so that when enabled, the hydroxyl radicals are generated. Hydroxyls are reactive and short lived, however the closed housing reaction chamber preferably has polygonal interior walls, so that the hydroxyl radicals will bounce against the walls so as to decontaminate within the reaction chamber as well as downstream in open air areas. Breathable air is then directed through the closed housing, so that the created and excited radicals will react quickly to air and surface impurities, such as pathogens and VOC's, rendering them neutral.

The UV optics are tubular, medical grade pure quartz. The optics are designed to emit/irradiate Ultraviolet irradiation in the nanometer wavelength/Ultraviolet spectrum of between 100 and 400 nanometers.

A multi wave 'Harmonic' is created via a multiwavelength nanometer configured optic irradiation. This configuration results in the creation of the desired atmospheric hydroxyl within the hydroxyl generator reaction chamber, which is a multi-sided reaction chamber, designed in such a way as to optimize atmospheric downstream hydroxyl production, such as for example in a polygonal-shaped housing. This multi-sided reaction chamber enables the desired atmospheric hydroxyl to be injected downstream to affect positive change. The positive change is the control/neutralization of pathogens and VOC's.

The —OH formed hydroxyl molecule is the capacitor that donates electrons to the targeted pathogen, whereupon the pathogen is therefore neutralized by the 'Electron Voltage (eV')' capacitance carried by the hydroxyl. The eV is donated at the point of contact with the pathogen.

VOC's are neutralized through the action of Bond Dissociation Energy (BDE). The capacitance of the charged hydroxyl is sufficient so as to take out of phase (decomposition) of any airborne molecular or compound structure. In Phase VOC chemistry can be harmful, therefore out-of-phase atomic airborne structures are now neutral and cannot recombine. The exception to this rule would be the recombination of water vapor, carbon dioxide and lastly oxygen (O2).

This reaction sequence is essential to all life, in that water vapor feeds all life, and carbon dioxide (CO2) is necessary/essential for plant life and oxygen (O2) is essential for air breathers such as humans, other animals and forms of living organisms.

Because exposure of the UV light is problematic for human eyes, the interior of the reaction chamber is custom designed to arrest UV light escaping and to maximize atmospheric hydroxyl discharge. Refraction color can come out of the unit with the generated, activated hydroxyls, but never direct UV light.

Available hydrogen is low in our natural environment, so one must add electron rings to obtain optimal amplitude as opposed to adding hydrogen for increased hydroxyl production.

The polygonal shape of the reaction chamber enhances the total ability of the chamber to produce the desired atmospheric hydroxyl.

It is essential that the atmospheric hydroxyls be produced by the exposure of ambient water vapor within a confined refractive generator chamber housing to prevent diminution of the atmospheric hydroxyls. In contrast, SanUVox, by using outward facing reflectors but no confined generator chamber housing, causes a drastic diminution of the desired hydroxyl production.

In contrast the present invention, by using the polygon shaped reaction chamber, has categorically enhanced atmospheric hydroxyl production.

Because exposure of the UV light is problematic for human eyes, the interior chamber holding the reaction chamber is custom designed to arrest UV light escaping and to maximize atmospheric hydroxyl discharge. Refraction color can come out of the unit with the generated, activated hydroxyls, but never direct UV light.

Available hydrogen is low in our natural environment, so one must add electron rings to obtain optimal amplitude as opposed to adding hydrogen for increased hydroxyl production.

The polygonal shape of the reaction chamber enhances the total ability of the chamber to produce the desired atmospheric hydroxyl.

However, in small environments, such as in a self-contained unit in a transit vehicle (passenger rail, passenger bus, trucking cargo shipping, etc.), or in a portable room size self-contained unit (movable with casters or wheels, or stationary mounted to a room surface, such as a wall), a fan is necessary to pull the ambient air with water vapor into the polygonal hydroxyl generator with a UV quartz optics, so that the water vapor molecules become hydroxyl radicals and thereafter are pushed by the fan out of the self-contained and/or portable unit.

For safety, an air pressure safety switch is provided, so that when air flow is not detected, this unit will be dormant. A Micro Switch shuts down all systems should the device be opened when unit is in the ON/RUN position.

Building Duct HVAC Device and System

The building HVAC duct hydroxyl generating units also have communications capabilities, so that the Hydroxyl Generating Device can interface with a remote-control pad or mobile phone.

Safety features include a microswitch which will shut off from inadvertent opening if the reaction chamber device is "on" when it should be "off". The micro switch shuts down all systems should the device be opened when the generating unit is in operational status.

Anti-Vibration G-Force Mitigation Clips are installed, such as spring clips which operate in only one directional installation.

Reactor Rod Safety is paramount, for prevention of Reactor Rod displacement and breakage.

The building HVAC duct hydroxyl generating unit also includes custom designed noise reduction adhesive pads, and strategically placed self-adhesive sound/vibration reduction material wall insulation to mitigate sound and vibration.

Building HVAC units in general have the above features, but where the optics are provided in a two optic array of a-b options, where "A" is on, but "B" is on if A fails.

No fan assembly is needed because the HVAC system has its own air movement capability. In a double optic option one optic may be on to create the hydroxyl radical and the existing HVAC fan directs the hydroxyls with the dual optic availability, should there be an abnormal intrusion of VOCs' or pathogens into the HVAC system, then the sensor would alert the hydroxyl device and the second optic would then come online in order to neutralize the threat load.

For safety, an air pressure safety switch is provided, so that when air flow is not detected, this unit will be dormant.

A Micro Switch shuts down all systems should the device be opened when unit is in the ON/RUN position.

In summary the hydroxyl generator includes a housing having an air inlet at one end and air outlet at an opposite end thereof, wherein the housing contains a plurality of spaced crystal-spliced UV optics, the UV optics being tubular, medical grade pure quartz optics designed to emit/irradiate ultraviolet in the nanometer wavelength/ultraviolet spectrum of between 100 and 400 nanometers for deactivating chemicals and pathogens in the breathable air for the respective flight deck and passenger compartments, on mass transit rail and road vehicles, in building ducts and other human occupied spaces. The air inlet at one end and the air outlet at an opposite end of the housing are provided for exposing ambient water vapor to the plurality of spaced crystal-spliced UV optics, to generate the hydroxyls. Preferably, the housing comprises a lengthwise extending hollow housing having a polygon shape in cross section, with adjoining lengthwise extending flat walls.

BRIEF DESCRIPTION OF THE DRAWINGS

The present invention can best be understood in connection with the following drawings, which are not deemed to be limiting in scope.

FIG. 5A is a flow chart showing the electronic controls with respect to their position adjacent to the hydroxyl generator.

FIG. 11 is a computer screen shot image of data associated with the Wi-Fi network of FIG. 9.

DETAILED DESCRIPTION OF THE DRAWINGS

As used throughout this specification, the word "may" is used in a permissive sense (i.e., meaning having the potential to, or being optional), rather than a mandatory sense (i.e., meaning must), as more than one embodiment of the invention may be disclosed herein. Similarly, the words "include", "including", and "includes" mean including but not limited to.

The phrases "at least one", "one or more", and "and/or" may be open-ended expressions that are both conjunctive and disjunctive in operation. For example, each of the expressions "at least one of A, B and C", "one or more of A, B, and C", and "A, B, and/or C" herein means all of the following possible combinations: A alone; or B alone; or C alone; or A and B together; or A and C together; or B and C together; or A, B and C together.

Also, the disclosures of all patents, published patent applications, and non-patent literature cited within this document are incorporated herein in their entirety by reference. However, It is noted that the citing of any reference within this disclosure, i.e., any patents, published patent applications, and non-patent literature, is not an admission regarding a determination as to its availability as prior art with respect to the herein disclosed and claimed apparatus/method.

Furthermore, any reference made throughout this specification to "one embodiment" or "an embodiment" means that a particular feature or characteristic described in connection therewith is included in at least that one particular embodiment.

Thus, the appearances of the phrases "in one embodiment" or "in an embodiment" in various places throughout this specification are not necessarily all referring to the same embodiment. Therefore, the described features, advantages, and characteristics of any particular aspect of an embodiment disclosed herein may be combined in any suitable manner with any of the other embodiments disclosed herein.

Figures 1, 2:
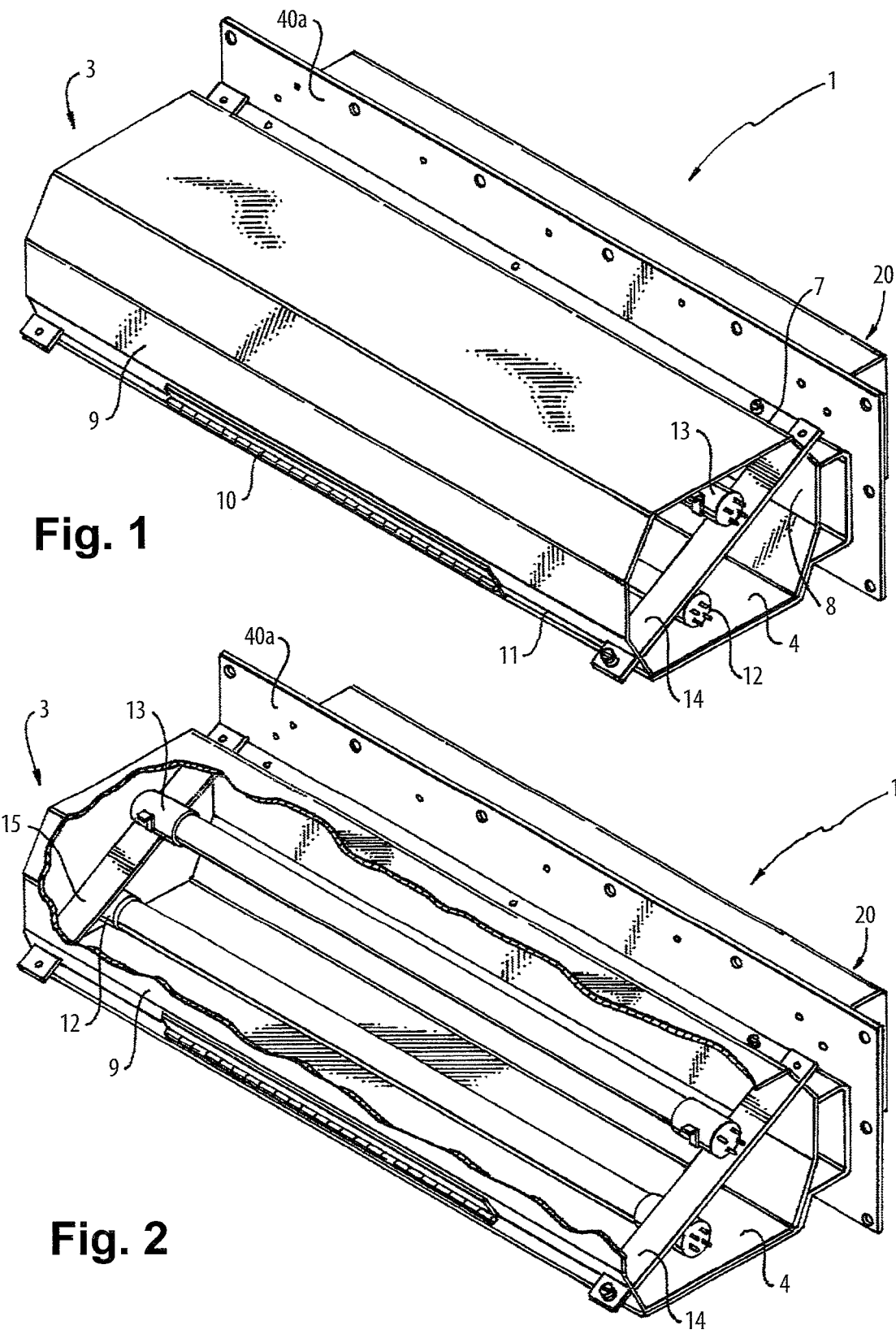
FIG. 1 is a perspective view of a polygonal hydroxyl generator shown in a closed position.
FIG. 2 is a perspective view of the hydroxyl generator of FIG. 1 shown in partial crossection with an open view of the interior of the hydroxyl generator.
Figure 4:
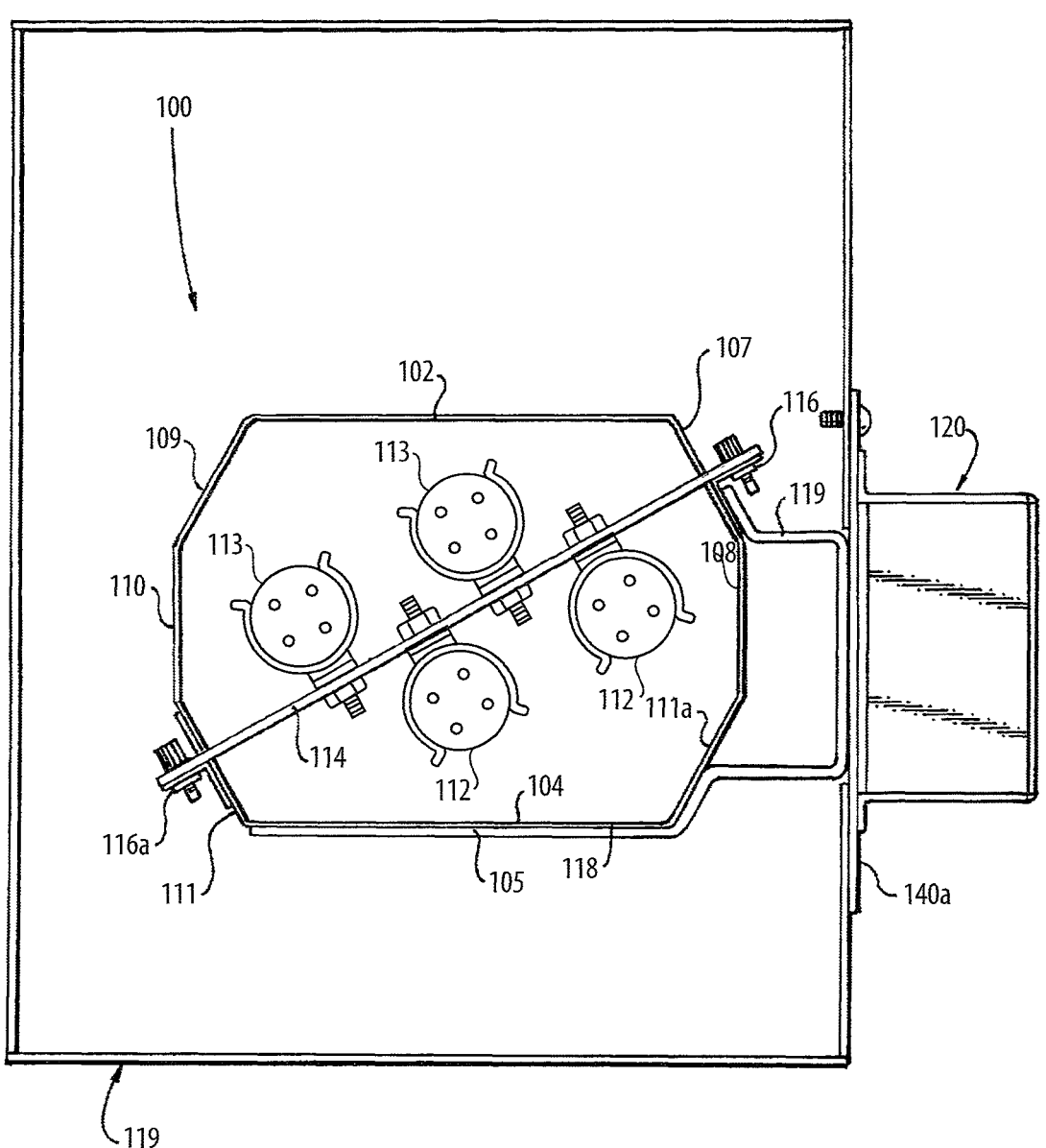
FIG. 4 is a crossectional end view of an alternate embodiment for a hydroxyl generator, showing four UV hydroxyl generator optics within the polygonal hydroxyl generator.

FIG. 1 shows a hydroxyl generator 1, including a polygonal-shaped housing, including a bracket brace 14 for crystal-spliced UV optics 12 and 13 (and a bracket 114 for UV optics 112, 112a, 113, and 113a shown in FIG. 4), which crystal-spliced UC optics are mounted parallel to each other inside the clamshell hexagon housing, wherein the crystal spliced UV optics 12 and 13 each have a length that runs substantially the entire length of the housing of the hydroxyl generator 1. As shown in FIG. 4, the generator mounting bracket 119 may be formed with a first flange, and a second flange and a third flange each extending perpendicularly away from respective distal ends of the first flange for thereby forming a channel-shaped cross-section, and with a fourth flange extending away from a distal end of the second flange, a fifth flange extending away from a distal end of the third flange, and a sixth flange extending away from the end of the fifth flange, where the third flange and the fourth flange may be at angles matching first and second sides of the octagonal-shaped housing, and the sixth flange may be at an angle matching and supporting a bottom of the housing. A preferred example for the crystal-spliced UV optics 12 and 13 is the GPH457T5L/4P UV Optic 4-pin Base 18" GPH457T5 of Light Spectrum Enterprises of Southampton these optics 12 and 13 are typically 18 inches long and are made of quartz. The tubular optics 12 and 13 are composed of pure Medical Grade quartz crystal in the portion of the optics which creates the hydroxyls. The present invention adds additional frequencies to the pure crystal optics. This tubular lamp optics 12 and 13 generate 'Harmonic' bio-mimicry nonchemical process of the present invention enables the production of desired atmospheric hydroxyls at a rate commensurate with the VOC/Bio loading in that particular space to be treated with the hydroxyls.

In contrast to the medical grade quartz tubular optics, it is noted that total glass tubes cannot be used when generating UV. The glass would simply be vaporized. Some companies use a fusion of glass and quartz crystal, which is not optimal as the glass portion creates a frequency that actually attracts contaminants. This problematic action neutralizes the desired UV action. Such a fusion lamp of glass and quartz crystal is cheaper to produce, however the poor performance of the lamp would be the end result.

Figure 3:
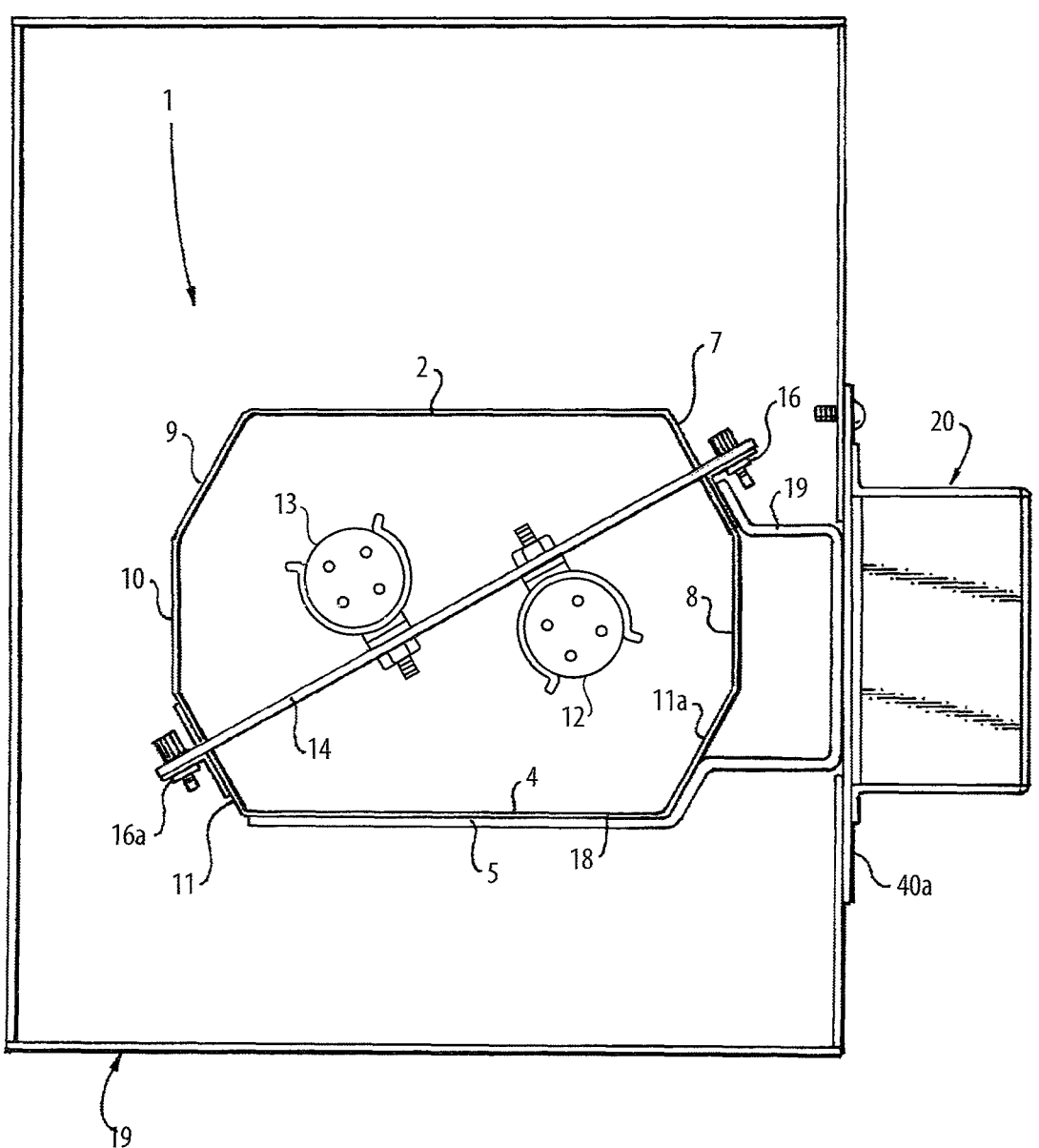
FIG. 3 is an end view in crossection of the hydroxyl generator of FIG. 1, with two UV optics for generating hydroxyl radicals.

Other similar Medical Grade quartz tubed UV optics can be used. The optics 12 and 13 are preferably symmetrically positioned in the housing of the hydroxyl generator 1, as shown in FIGS. 3 and 4 to operate most efficiently, but where in FIG. 3 the crystal spliced UV optics 12 and 13 are staggered so that UV optic 12 is on a different side of the bracket brace 14 from the side on which UV optic 13 is located. FIG. 4 shows an alternate embodiment where there are two pairs of UV optics, namely 112,113 and 112a, 113a. The UV optics 112, 113 are staggered to the right on one bottom side of the horizontal bracket brace 114, but are separated by upright bracket brace 114. Likewise, UV optics 112a and 113a are respectively staggered to the left on the opposite top side of the horizontal bracket brace 114, also separated from each other by upright bracket brace 114. Optics pairs 112, 112a and 113, 113a are supported within pairs of respective C-shaped spring clasps 112c, 113c and 112d, 113d, which pairs of optics 112, 112a and 113, 113a are each respectively mounted on bracket brace 114, and which pairs of optics 112, 112a and 113, 113a are mounted parallel lengthwise to each other inside the clamshell hexagon housing 1.

The clamshell hexagon housing hydroxyl generator 1 has a clamshell configuration, including a clamshell top wall 2, upper side walls 7, 8, 9 and 10, fasteners 16a, 16a, a hinge 6 for opening the polygonal clamshell housing 1 and a bottom clamshell portion, including a bottom wall 4 and angle-oriented walls 11 and 11a, whereby the polygon housing opens hinge 6 to expose the inside of the hydroxyl generator 1 for maintenance and/or repair. In addition, the polygon hydroxyl generator enclosure can be removed from the air duct wall 40A for such maintenance and repair. The hydroxyl generator also includes an adjacent electronic control box 20, which is attachable to the clamshell housing of the hydroxyl generator 1. Alternatively, as shown in FIGS. 3 and 4, the electronic control box 20 is preferably located outside of the air path, which may be a duct or other conduit. It can alternatively be attached outside of the duct. It communicates with the UV optics wirelessly. The reason for the polygon shape is that the hydroxyl generators generated by the crystal-spliced UV optics 12 and 13 are scattered upon being generated by the optics 12 and 13, but they dissipate quickly if not activated by contact with reflective non-absorbent surfaces inside the respective walls of the polygon. The purpose of the polygon shape is that when the hydroxyl radicals are generated, they are emitted radially in all directions from the UV crystal-spliced optics 12 and 13 and normally would dissipate when scattered radially from the optics. In order to permit the hydroxyl radicals to maintain their desired electron charge and ability to contact and inactivate mold, volatile organic compounds, pathogens, bacteria, virus, etc., they need to reflect and refract off of the reflective non-absorbent walls continuously, within the reaction chamber confined space. As atmospheric hydroxyls are being activated by being created and excited in back-and-forth activity, the air inside the air duct/plenum 40a will contact the activated hydroxyl radicals with the end result of the neutralization of any impurities, such as VOCs, virus, bacteria, fungi, etc., in the air and surfaces.

Furthermore, once these radicals are emitted, they can penetrate any crevices in any area, such as in hydroponic greenhouse plant media growing vessels, such as between seats of aircraft, mass transit rail and road vehicles, in building ducts and wall surfaces and other human occupied spaces, such as individual rooms with small self-contained hydroxyl generators, between the surfaces of seats and shelving, and anywhere where ultraviolet light by itself would not be capable of eradicating the undesirable VOCs, fungi, virus, bacteria, etc. In the aircraft environment, the polygon-shaped housing is strategically located within an air supply unit in an airport terminal building, or it can be located within a remote cart not located near the aircraft, on the tarmac of the airport, and preferably it may be provided in the air systems separately of an aircraft cabin, including the flight deck and the areas of the main cabin where passengers are seated. Therefore, the polygon shaped housings may also be strategically located in mass transit rail and road vehicles, in building ducts, in individual rooms, and wall surfaces and other human occupied spaces As shown in the end view of FIG. 3, the inside of the polygon housing 1 is located below the field of vision within the sealed off plenum so that the ultraviolet (UV) crystal-spliced tubular optics 12 and 13 will not be exposed to the eyes of any observers. Therefore, while the hydroxyl radicals are being generated, the UV energy which create hydroxyl generation from optics 12 and 13 are completely sealed off so that when the optics 12 and 13 are operational, the UV light emanating therefrom will not penetrate outside of the polygonal housing. Baffles, optionally located outside of the hydroxyl generators, but in the vicinity of the hydroxyl generators, prevent the UV light from exposure to persons. Additionally, fibrous filters may be provided at input and outlet areas of the housing containing the hydroxyl generator portion with the UV optics, to capture any undesirable airborne particulates, such as dirt and dust and other particles which may compromise the sensitive quartz material of the UV optics. There is no restriction regarding the active flow of the hydroxyls inside the hydroxyl generator 1 and no interference with the excitement of the hydroxyls produced by the exposure of ambient water vapor within the polygon shaped housing with the UV optics 12 and 13 irradiating light that causes the —OH radicals to form.

FIG. 4 shows an alternate embodiment for a four optic version, where polygon hydroxyl generator enclosure 100, having top wall 102, side walls 107, 108, 109, 110 of an upper shell, as well as lower walls 105, 111a, 111b of the clamshell housing. The clamshell housing has inner walls 104 against which the hydroxyls being formed contact repeatedly during formation. FIG. 4 also shows the electronics control box 120, attached to the clamshell housing by brackets 119. The respective pairs of optics 112, 112, and 113, 113 are supported within respective pairs of C-shaped spring clasps, which are each respectively mounted on bracket brace 114, which are mounted parallel lengthwise to each other inside the clamshell hexagon housing 101. The upper half of the clamshell housing is connected to the lower half of the clamshell housing by fasteners 116, 116a. Clamshell housing 100 is openable via hinge located near fastener 116a.

Figure 5:
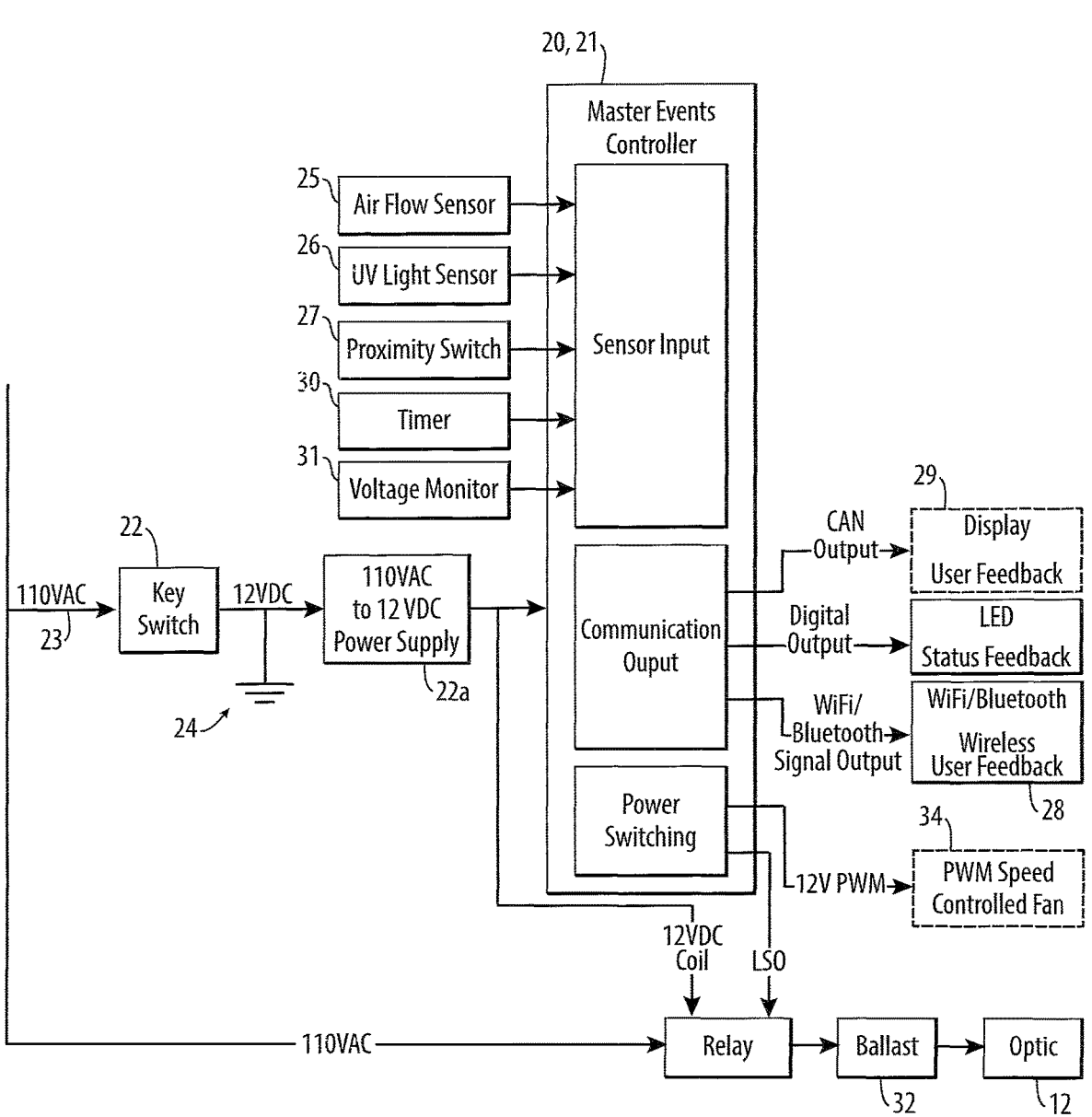
FIG. 5 is a block diagram of the electronic controls of the hydroxyl generator of FIGS. 1-3 and 4.

FIG. 5 is a block diagram showing the network and electronics of the control box 20. Initially AC power 23 of 110 VAC is converted by converter 22 to low voltage 12 VDC, or else a low voltage battery alternatively delivers 12 VDC to a secure Key Switch 22a, to provide power to the Master Events Controller 20, which may have a microprocessor 21. The Master Events Controller 20 also receives input from sensors, such as Air Flow Sensor 25, UV Light Sensor 26, Proximity Switch 27 (detecting opening of the enclosure), Timer 30 and Voltage Monitor Sensor 31. These sensors provide Sensor Input to the Master Events Controller 20. Power Switching in the Master Events Controller 20 sends 12V Pulse Width Modulation data to a PWM Speed Controlled Fan 34, to send air through the hydroxyl generator unit 1 or 101, or to stop the flow of air when needed for safety and maintenance situations. The Power Switching also sends data via a Large Serve Outlet (LSO) to a Relay, which controls the Ballast 32, providing power to the Crystal UV Optics 12, which creates the needed hydroxyls within the hydroxyl generators 1 or 101. The Master Events Controller 20 also has a Communications Output, which can send data via a Controller Area Network (CAN) to a Visual Display 29 for user feedback. The Communications Output of the Master Events Controller 20 also sends digital data wirelessly as output to Status Feedback Units. The Communications Output of the Master Events Controller 20 also sends Wi-Fi/Bluetooth® Signal output to Wireless input devices 28 for Wireless user feedback during use.

FIG. 5A is a diagrammatic flow chart, showing the electronic control box 20 of FIGS. 1, 2 and 3, which is also equivalent to the electronic control box 120 of FIG. 4. Adjacent to the hydroxyl generator 1 or 101, which in FIGS. 1-3, the hydroxyl generators are attached by one or more brackets 19 to the electronic control box 20. Similarly, the electronic control box 120 is attached by brackets 119 of FIG. 4.

In the diagrammatic flow chart of FIG. 5A, related to the electrical block diagram of FIG. 5, the control box 20 includes a microprocessor 21 for controlling the sensors and switches, which control the operation of the optics 12 and 13, or 112 and 113, of the hydroxyl generators 1 shown in FIGS. 1-3 and 4 respectively. There is also a power source being either a DC low-voltage battery 24, or an AC plug 23, to provide higher-voltage AC power. When the AC is used, a converter 22 can be provided to convert high-voltage AC to low-voltage DC power for operating any of the sensors and control elements within box 20. Box 25 of FIG. 5A discloses the detector 25 to detect whether airflow is on, so that the optics 12 and 13 will only be on after airflow is confirmed, so that they are not on when there is no airflow. Box 26 of the diagrammatic flow chart of FIG. 5A discloses the sensor 26 for detecting emitted light, and providing feedback to replace optics, including a secondary backup optic, which is also disclosed in box 26 of the flowchart of FIG. 5A. Box 27 of the diagrammatic flow chart of FIG. 5A discloses a detector with a proximity switch 27 detecting opening of the enclosure, and thereafter used to turn off the optics 12 and 13, to protect people from being exposed to the possible harmful UV light emitted from the optics 12 and 13. This detector with the proximity switch 27 shown in box 27 of the diagrammatic flow chart of FIG. 5A also includes a limit switch, a micro switch and sensors. Box 28 of the diagrammatic flow chart of FIG. 5A discloses the mobile phone application connection 28 for user feedback by wireless communication, such as Wi-Fi or Bluetooth® communications, between the operator, the control box 20 and hydroxyl generator 1 itself, together with a timer. The control box 20 also includes the LCD user feedback system 29, with a timer shown in box 29 of the diagrammatic flow chart of FIG. 5A with a timer, as well as a further timer 30 shown in box 30 of the diagrammatic flow chart of FIG. 5A, to provide feedback for regular maintenance. The voltage and frequency of AC main supply sensor 31 is shown in box 31 of the diagrammatic flow chart of FIG. 5A, Box 32 of the diagrammatic flow chart of FIG. 5A shows the voltage and frequency of the monitor of the ballast power outfit 32. Box 33 of the diagrammatic flow chart of FIG. 5A discloses a fire sensor 33, which detects excess heat in the system. Box 34 of the diagrammatic flow chart of FIG. 5A discloses a real time clock 34 which controls any fans providing and activating the airflow through the polygon hydroxyl generators 1.

Figure 5B:
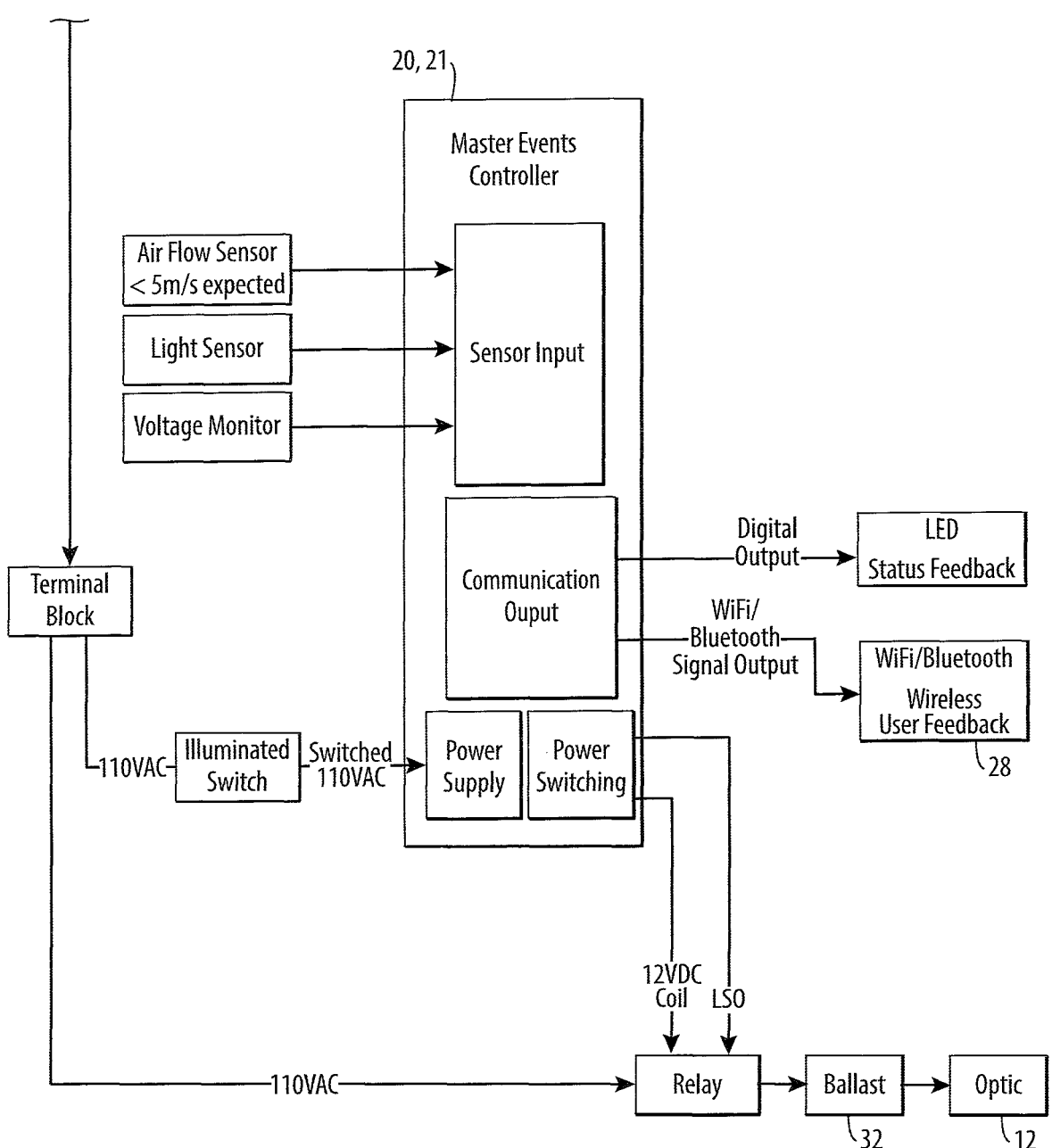
FIG. 5B is a block diagram of the electronic controls of the hydroxyl generator used in hydroponic greenhouse applications shown in FIGS. 6 and 6A, or in other applications requiring the electronic controls of FIG. 5B.

In the alternate embodiment shown in block diagram FIG. 5B, there are disclosed therein shown the following differences of block diagram FIG. 5B from block diagram FIG. 5, wherein in block diagram FIG. 5B the following features are shown:

1. The key switch (22a) can alternatively be positioned before the power supply (22);
2. The key switch (22a) can alternatively be a pushbutton;
3. The power supply (22) can alternatively be included in the Master Events Controller (MEC) 20;
4. The user feedback display (29) of FIG. 5 is not needed in FIG. 5B, because the Wi-Fi/Bluetooth® communication works with a mobile application;
5. The PWM Speed controlled fan (34) of FIG. 5 is not needed, because the hydroxyl generator 1 will be located in an existing duct with moving air; and,
6. The power to the relay (not numbered) in FIG. 5 can alternatively be provided by the Master Events Controller (MEC) 20 in FIG. 5B.

EXAMPLE

Building Duct HVAC Embodiment

Figure 8:
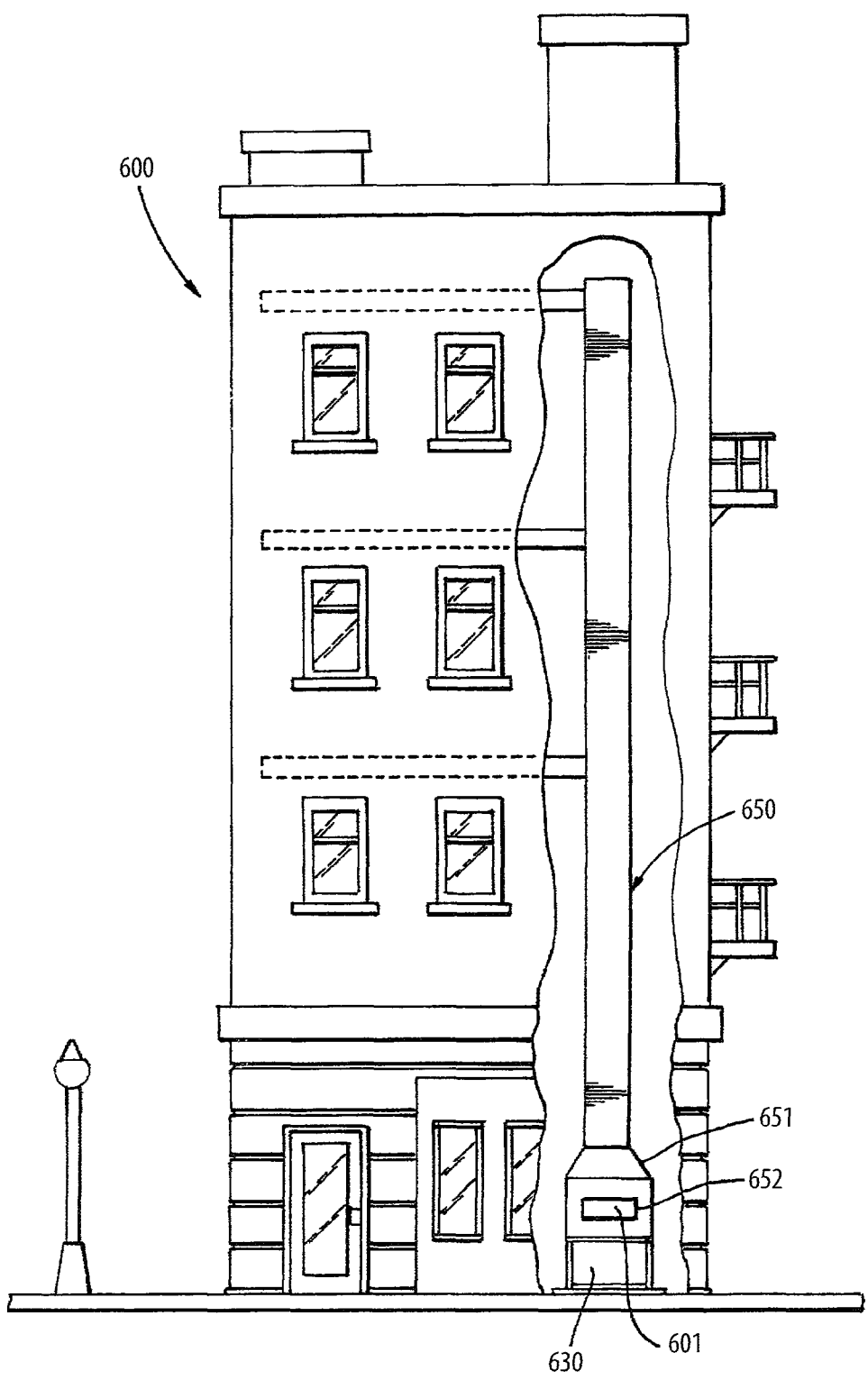
FIG. 8 is a diagrammatic environmental view in partial cross section of a building having a duct having a wall into which is installed a radical hydroxyl generator, wherein the duct is a part of a heating, ventilation air conditioning (HVAC) unit through which breathable air with water vapor flows.

In the building duct environmental view of FIG. 8, a multi-story building 600 is shown in partial cutaway cross section. FIG. 8 shows a diagrammatic environmental view in partial cross section of a building having a duct 650 having a wall 651 into which is installed a radical hydroxyl generator, wherein the duct is a part of a heating, ventilation air conditioning (HVAC) unit through which breathable air with water vapor flows. Secondary air flow ducts are shown at the manifold joints with the main air duct 650.

Figure 5C:
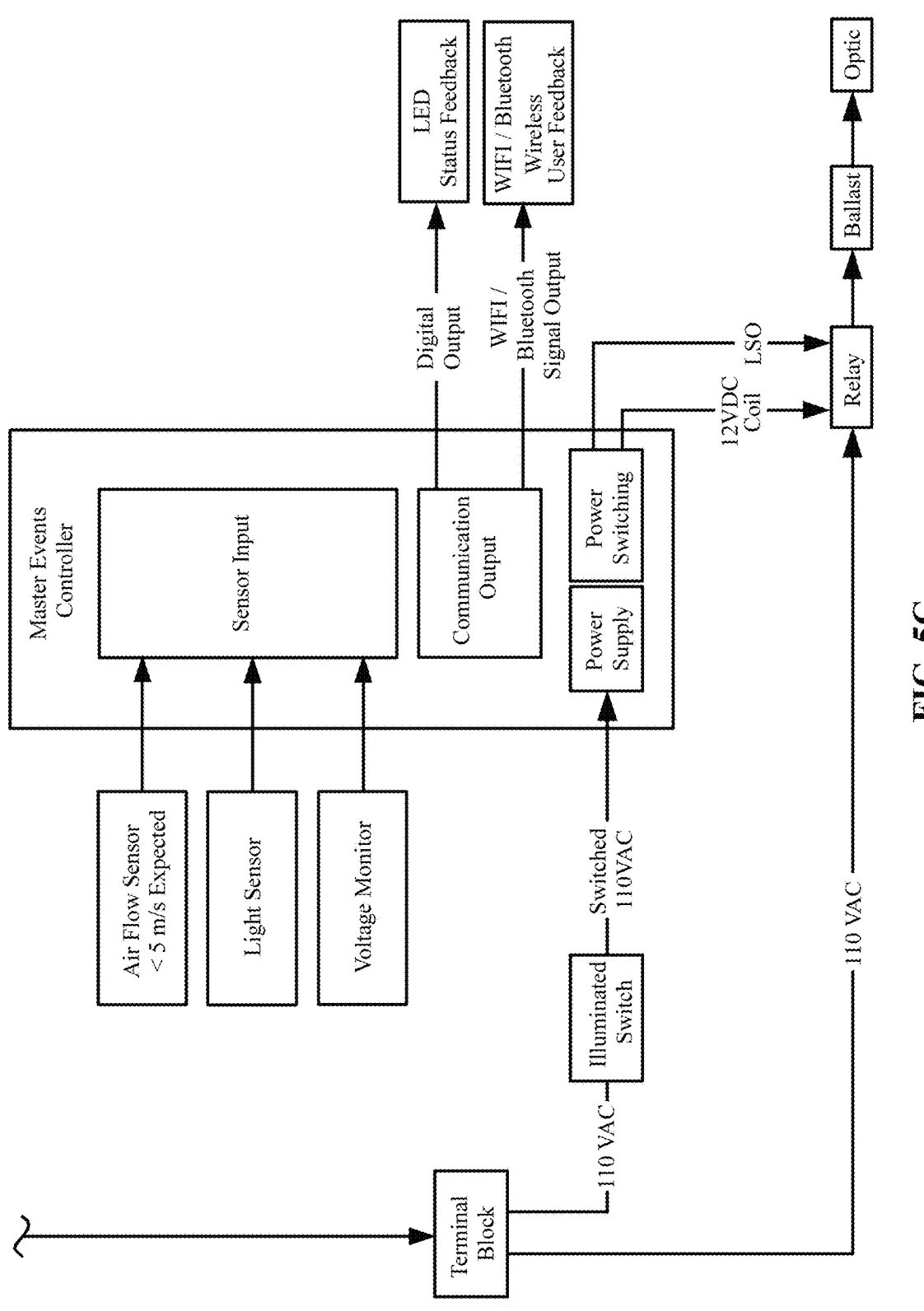
FIG. 5C is a block diagram of the electronic controls of the hydroxyl generator used in HVAC building duct applications, or in other applications requiring the electronic controls of FIG. 5C.
Figure 5D:
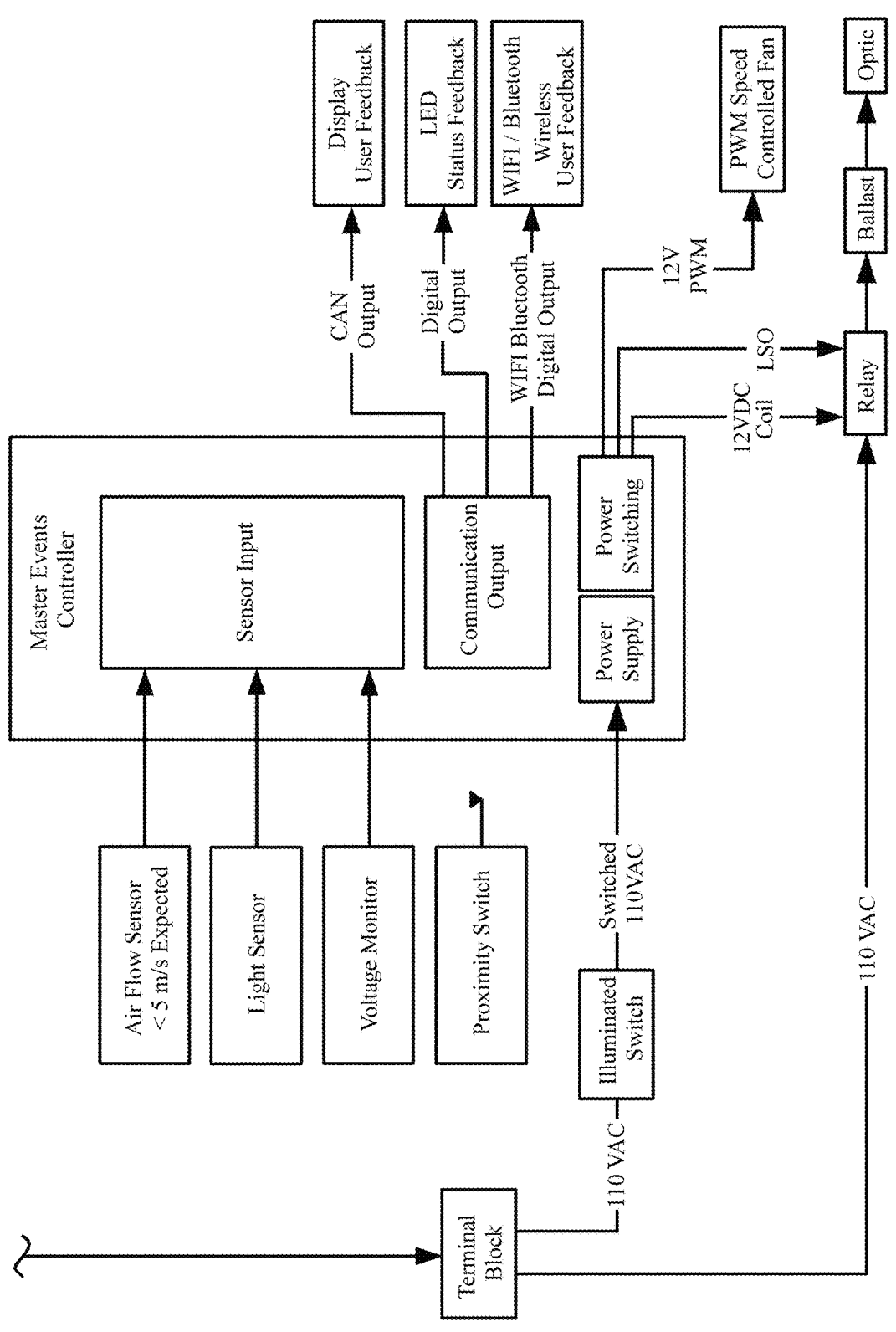
FIG. 5D is a block diagram of the electronic controls of the hydroxyl generator used in Portable Room-Sized Unit applications, or in other applications requiring the electronic controls of FIG. 5D, which include a proximity detector for safety reasons and a fan, such as a pulse width modulated fan, which regulates the air speed of the fan by regulating the voltage of the fan between on and off, to move air flow with air purifying generated hydroxyl radicals therethrough.

FIG. 5C, similar to the block diagram of FIG. 5B, is a block diagram of the electronic controls of the hydroxyl generator used in HVAC building duct applications, or in other applications requiring the electronic controls of FIG. 5C.

Figures 6, 6A:
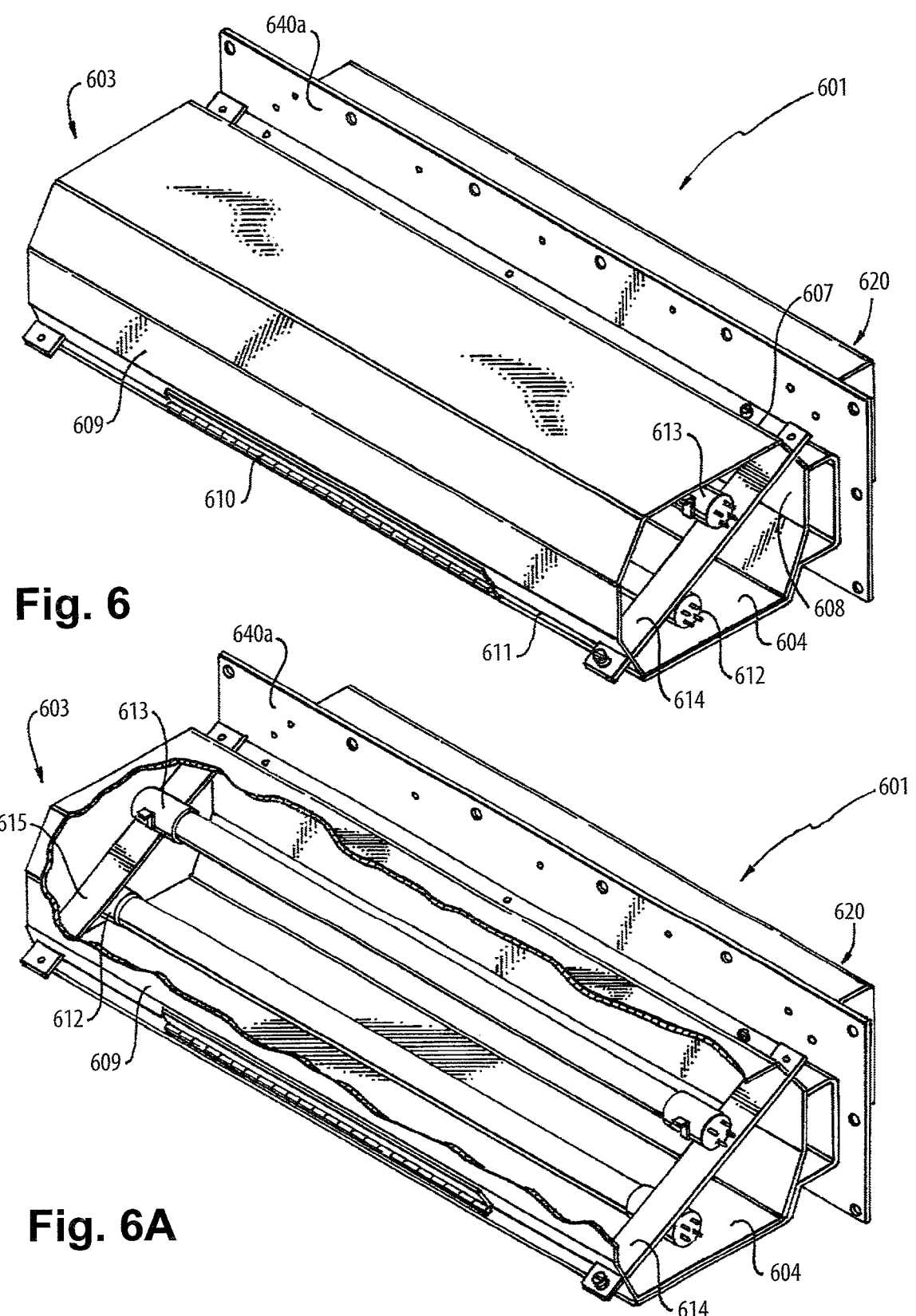
FIG. 6 is a perspective view of hydroxyl generator for a building having a HVAC unit duct embodiment, to be installed within the building HVAC unit air flow duct, to provide hydroxyl radicals for ambient, heated or cooled breathable air flowing therethrough.
FIG. 6A is a perspective view in partial cutaway of the polygonal hydroxyl generator shown in FIG. 6.
Figure 6B:
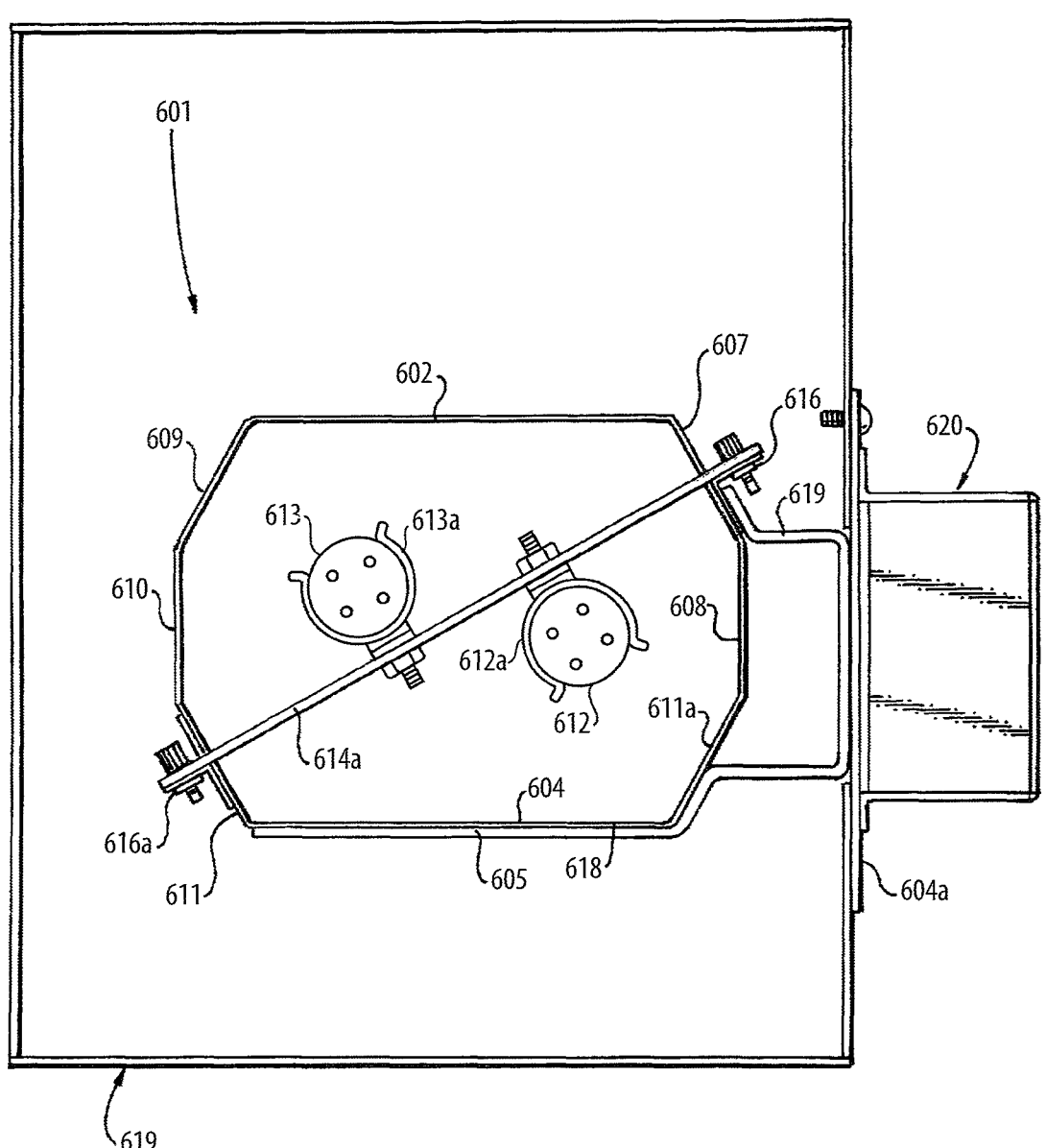
FIG. 6B is an end view in cross section of the hydroxyl generator of FIG. 6, with two UV optics for generating hydroxyl radicals.

As also shown in FIG. 8, air flow duct 650 has walls 651, etc., where the duct 650 is connected to a HVAC unit 630, which provides respective heated, ambient, or cooled breathable air. An air purification hydroxyl producing unit 601 as in FIGS. 6, 6A and 6B, is provided inside of duct 650 of FIG. 8, so that water vapor in air flowing therethrough will contact with the light emanating from optics 612, 613, and upon contact therewith, will generate hydroxyl radicals to purify the air within building duct 650 . . . . Similarly, an air purification hydroxyl producing unit 601a as in FIG. 7, with multiple pairs of optics 612, 613, 612a, 613a, etc., could be also provided inside of duct 650 of FIG. 8, so that water vapor in air flowing therethrough will contact with the light emanating from multiple pairs of optics 612, 613, 612a, 613a, etc., upon contact therewith, will also generate hydroxyl radicals to purify the air within building duct 650 of the building 600 in FIG. 8.

Figure 7:
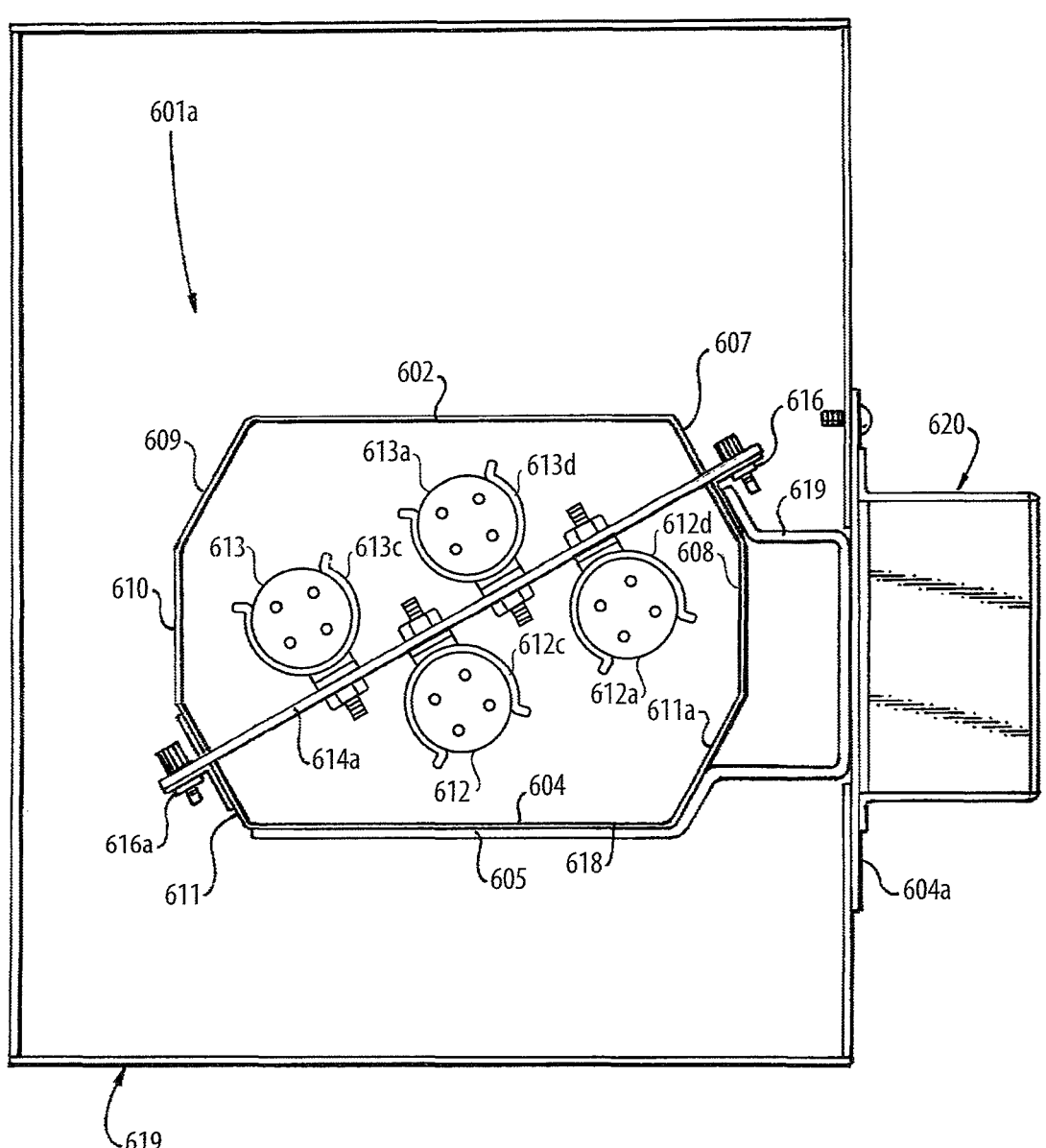
FIG. 7 is a diagrammatic end view in cross section view of an alternate embodiment for a building with an HVAC unit duct, showing a hydroxyl generator with multiple pairs of optics, for treating breathable HVAC unit ambient, heated, or cooling air flowing therethrough.
Figures 16, 16A, 16B:
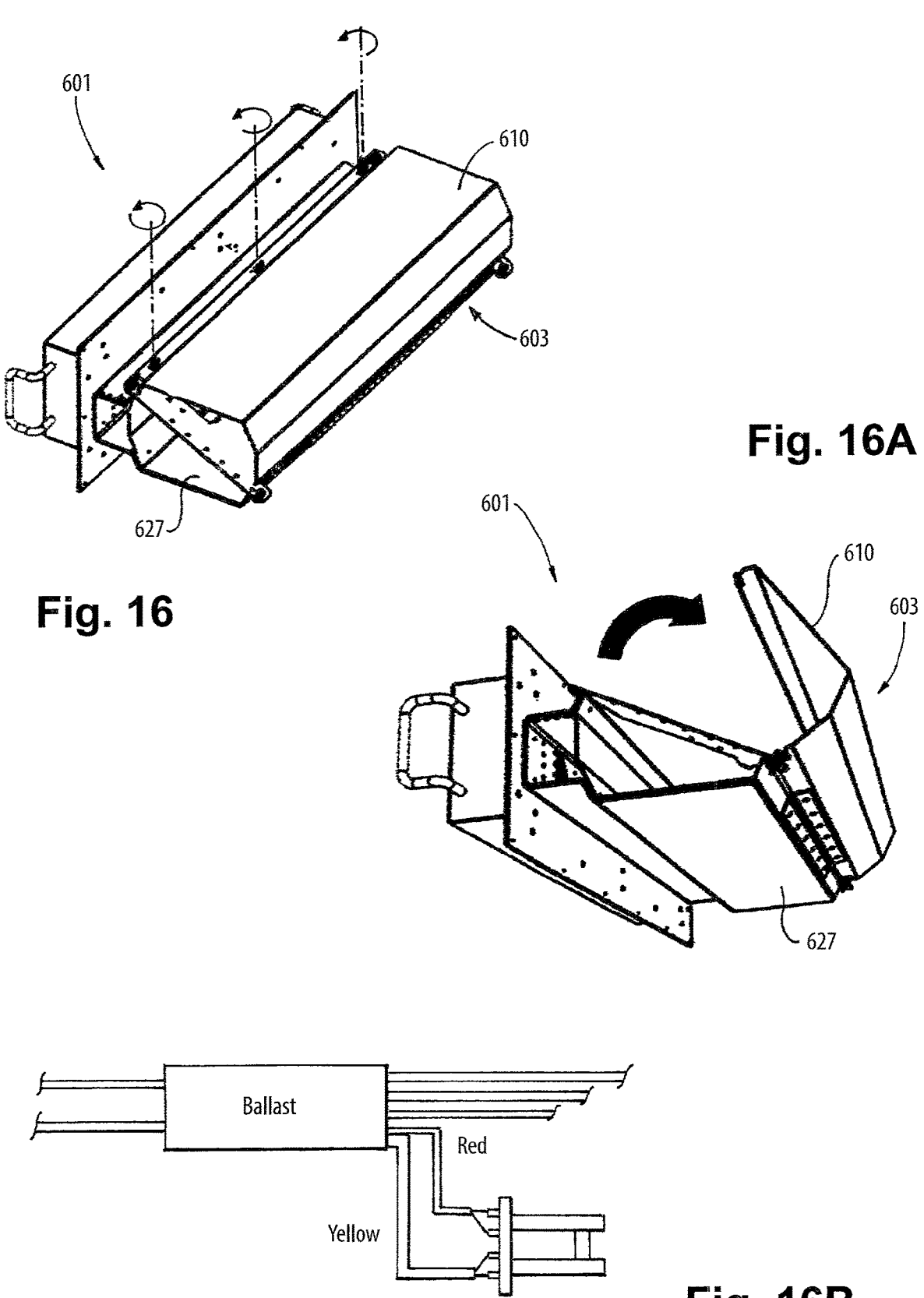
FIG. 16 is a perspective view of the hydroxyl generator installed as in FIGS. 13, 13A, 14 and 15 where arrows indicate fasteners to be released for pivotable opening of the hydroxyl generator.
FIG. 16A is a perspective view from below, showing the pivoted opening of the clamshell configuration of the hydroxyl generator of FIGS. 13, 13A, 14, 15, 16 and 16A, where the curved arrows indicate the pivoted opening of the clamshell housing of the hydroxyl generator.
FIG. 16B is a diagrammatic close-up detail view of the connection of the wiring of the optics located within the hydroxyl generator as in FIGS. 13,13A, 14, 15, 16 and 16A herein.

FIGS. 6, 6A and 6B show a building duct 650 with a support wall 651, having an HVAC unit duct hydroxyl generator 601, similar to hydroxyl generator 1 shown in FIGS. 1-3 with a pair of optics 612, 613. FIG. 7 shows an alternate embodiment, similar to the hydroxyl generator as in FIG. 4, for a hydroxyl generator 601A with two pairs of oppositely situated optics, attached to duct wall 651 of building duct 650 of building 600 shown in FIG. 8 herein. The hydroxyl generator 601 or 601a has a hinged polygonal shaped housing 603, which is openable in a hinged clamshell configuration, with a upper portion 610 of clamshell housing 603 having holes for attachment fasteners at a distal end of the upper portion, connected to a structural bracket 619 attached to front frame 640 of hydroxyl generator 601 or 601a and, as shown in FIGS. 16 and 16A, upper portion 610 is separated by a hinge at its proximal edge from a stationary bottom portion 627 of the clamshell housing 603 of the hydroxyl generator 601 or 601a.

As further shown in FIGS. 6, 6A and 6B, the hydroxyl generator 601 also includes the polygonal-shaped clamshell housing 603, including bracket braces 614, 615, for supporting crystal-spliced UV optics 612 and 613 within respective fasteners, such as C-shaped spring clasps 612a and 613a, which are each respectively mounted on brackets 614, 615 and which are mounted parallel lengthwise to each other inside the clamshell hexagon housing, but staggered so that UV optic 612 is on a different side of the brackets 614, 615 from the side on which UV optic 613 is located. The crystal spliced UV optics 612 and 613 each have a length that runs substantially the entire length of the housing of the hydroxyl generator 601. Similar to optics 12 and 13 of FIGS. 1-3, a preferred example for the crystal-spliced UV optics 612 and 613 is also the GPH457T5L/4P UV Optic 4-pin Base 18" GPH457T5 of Light Spectrum Enterprises of Southampton, which optics 612 and 613 are typically 18 inches long and are made of quartz. The tubular optics 612 and 613 are also composed of pure Medical Grade quartz crystal in the portion of the optics which creates the hydroxyls. The present invention adds additional frequencies to the pure crystal optics. Similar to optics 2 and 13 of FIGS. 1-3, the tubular lamp optics 612 and 613 of FIGS. 6, 6A and 6B generate 'Harmonic' bio-mimicry nonchemical process of the present invention enables the production of desired atmospheric hydroxyls at a rate commensurate with the VOC/Bio loading in that particular space to be treated with the hydroxyls.

Likewise, as shown in FIG. 7, in certain power situations, instead of using a pair of oppositely positioned optics 612 and 613 upon a brace 614, in certain situations two pairs of optics 612, 612 and 613, 613 may be employed in polygonal shaped hydroxyl generator 601a of FIG. 7, similar to hydroxyl generator 100 with two pairs of optics 112, 112, 113 and 113 as in FIG. 4.

Other similar Medical Grade quartz tubed UV optics can be used in the building HVAC unit ducting of building 600 shown in FIG. 8. For example, the optics 612 and 613 are preferably symmetrically positioned in the housing of the hydroxyl generator 601, as shown in FIG. 6, 6A and 6B to operate most efficiently, where in FIG. 6B the crystal spliced UV optics 612 and 613 are staggered so that UV optic 612 is on a different side of the bracket brace 614 from the side on which UV optic 613 is located.

In the alternate embodiment shown in FIG. 7, where there are two pairs of UV optics, namely 612, 612a and 613, 613a within hydroxyl generator 601a, the UV optics 612, 612a of polygonal hydroxyl generator 601a are similarly staggered to the right on one bottom side of the horizontal bracket brace 614a, but are separated by upright bracket brace 614a. Likewise, as also shown in FIG. 7, UV optics 613 and 613a are respectively staggered to the left on the opposite top side of the horizontal bracket brace 614a, also separated from each other by upright bracket brace 614a.

Optics pairs 612, 612a and 613, 613a of FIG. 7 are supported within pairs of respective fasteners, such as C-shaped spring clasps 612c,613c and 612d, 613d, which pairs of optics 612, 612a and 613, 613a are each respectively mounted on bracket brace 614a, and which pairs of optics 612, 612a and 613, 613a are mounted parallel lengthwise to each other inside the hinged clamshell hexagon housing.

Similar to the clamshell polygonal configurations of hydroxyl generators 1 and 100 of FIGS. 1-3 and 4, as shown herein in FIGS. 6, 6A, 6B, 16 and 16A, the clamshell hexagon housing hydroxyl generator 601 has a clamshell configuration, including a clamshell top wall 602, upper side walls 607, 608, 609 and 610, a hinge (shown in partial cross section in FIGS. 6 and 6A, and in FIGS. 16 and 16A) at the bottom edge of top clamshell portion 610) for opening the top 610 of polygonal clamshell housing 601 and a bottom clamshell portion 627 (shown in FIGS. 16 and 16A), including a bottom wall 604 and angle-oriented walls 611 and 611a, whereby the polygon housing opens at the hinge between top half 610 and bottom half 627 of clamshell housing 603 of hydroxyl generator 601, to expose the inside of the hydroxyl generator 601 for maintenance and/or repair of the hydroxyl generator of 601 located within duct 650 of building 600 shown in FIG. 8.

In addition, the polygon hydroxyl generator enclosure can be removed from the air duct wall 651 for such maintenance and repair, but only when power is shut off, so that maintenance personnel are not exposed to visually harmful beams from optics 612 and 613.

Figures 13, 13A, 14, 15:
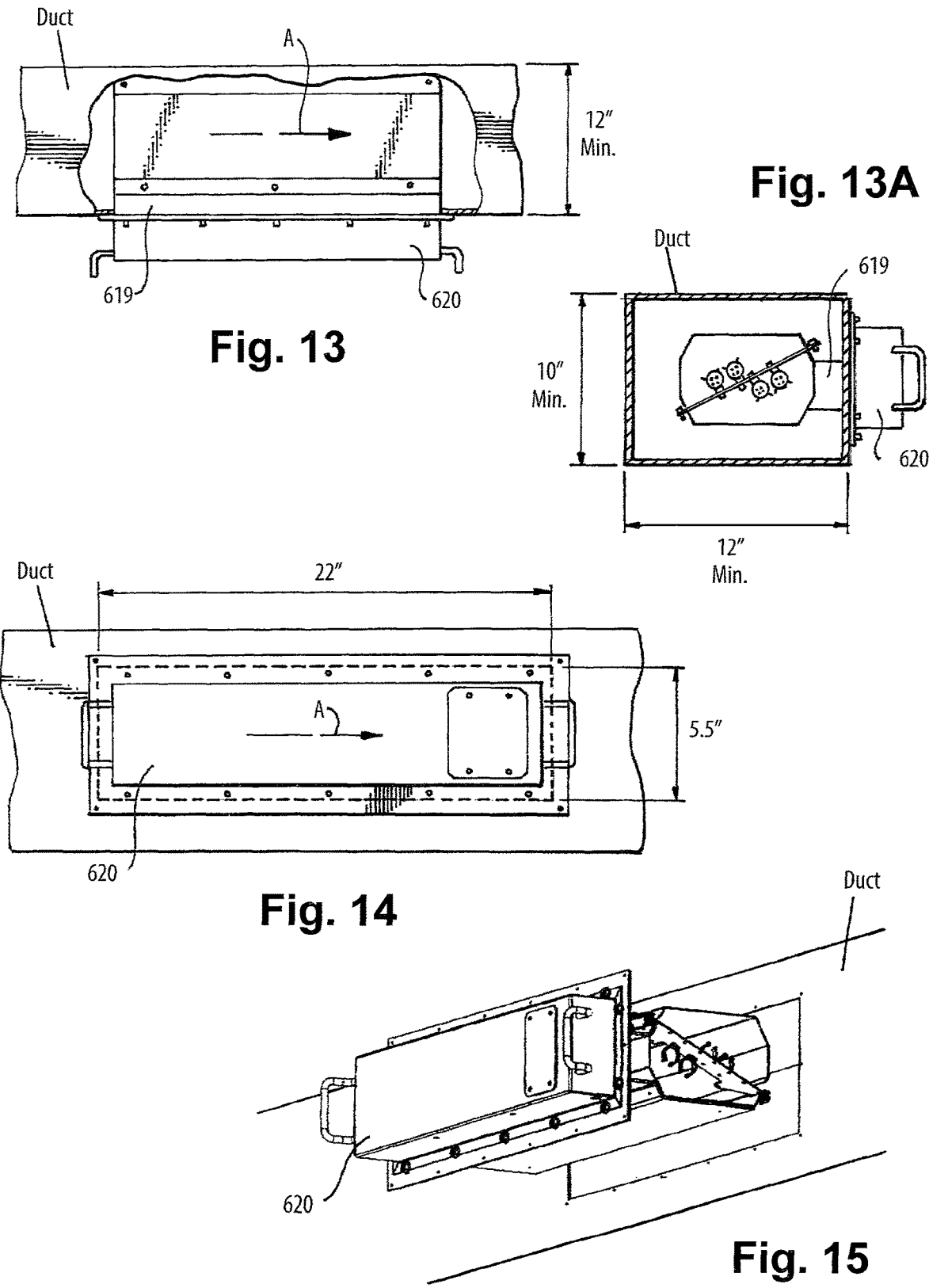
FIG. 13 is a close-up top plan view of a radical hydroxyl generator installed within a building duct as in FIG. 8, with an arrow indicating air flow therethrough.
FIG. 13A is a side elevation view of the radical hydroxyl generator installed within a building duct as in FIG. 13.
FIG. 14 is a front elevation view of the hydroxyl generator of FIGS. 13 and 13A, showing a rectangular cut out in a wall of the building HVAC unit duct, showing a vertical height of the duct opening and a lengthwise width of the duct opening, wherein an arrow indicated the direction of air flow with water vapor through the radical hydroxyl generator.
FIG. 15 is an exploded perspective view from below of the hydroxyl generator being installed into the cut-out of the building HVAC unit duct wall as in FIGS. 13, 13A and 14, showing the cut-out hole for insertion of the hydroxyl generator therethrough.

Similar to hydroxyl generator 1 of FIGS. 1-3, the hydroxyl generator 601 also includes an adjacent electronic control box 620, which is attachable to the clamshell housing of the hydroxyl generator 601, or provided in the vicinity thereof. Alternatively, the electronic control box 620 is preferably located outside of the air path, which may be the building HVAC unit duct or other conduit, where it can optionally be attached outside of the duct 650, wherein the control box 620 communicates with the UV optics 612, 613 wirelessly (or to optics 612, 612a, 613, 613a of a four bulb configuration). As shown in FIG. 13A and FIG. 15, the electronic control box 620 may have a first handle and a second handle.

The reason for the lengthwise extending polygon shape of the clamshell reactor housing 601 is that the hydroxyls generated by the crystal-spliced UV optics 612 and 613 could be scattered upon being generated by the optics 612 and 613, and theoretically dissipated quickly, if not activated by constant repetitive contact with reflective non-absorbent surfaces inside the respective walls of the polygonal shaped housing of hydroxyl generator 601 or 601a.

Therefore, the purpose of the polygon shape is that when the hydroxyl radicals are generated, they are emitted radially in all directions from the UV crystal-spliced optics 612 and 613 and normally would dissipate when scattered radially from the optics 612 and 613 (or to optics 612, 612a, 613, 613a of a four bulb configuration). But, in order to permit the hydroxyl radicals to maintain their desired electron charge and ability to contact and inactivate mold, volatile organic compounds, pathogens, bacteria, virus, etc., the hydroxyls need to reflect and refract off of the reflective non-absorbent interior walls of hydroxyl generator 601 continuously, within the reaction chamber confined space of its respective polygonal shape, which may be hexagonal, octagonal or any other polygonal shape. As atmospheric hydroxyls are being activated by being created and excited in back-and-forth activity within the polygonal shaped hydroxyl generator 601, and upon existing therefrom, the humid molecules of air inside the air duct/plenum 651 will contact the activated hydroxyl radicals flowing out of the hydroxyl generator 601, with the end result of the neutralization of any impurities, such as VOCs, virus, bacteria, fungi, etc., in the air and surfaces.

Furthermore, once these hydroxyl radicals are emitted to the breathable air of the human inhabited building, they can penetrate any crevices in any area of the building interior having HVAC unit duct 650, such as between seats of building interior furniture, between the surfaces of building room desks; and cabinets, or in any crevice where ultraviolet light by itself would not be capable of eradicating the undesirable VOCs, fungi, virus, bacteria, etc. The polygon-shaped housing 601 is strategically located within an air duct wall of building duct 650, which can be in a building which has sub walls extending to various rooms in the building 600.

As also shown in the end view of FIG. 7, the inside of the polygon housing 601 is located below the field of vision within the sealed off plenum so that the ultraviolet (UV) crystal-spliced tubular optics 612 and 613 will not be exposed to the eyes of any observers. Therefore, while the hydroxyl radicals are being generated, the UV energy which create hydroxyl generation from optics 612 and 613 are completely sealed off so that when the optics 612 and 13 are operational, and the UV light emanating therefrom will not penetrate outside of the polygonal housing. There is no restriction regarding the active flow of the hydroxyls inside the hydroxyl generator 601 and no interference with the excitement of the hydroxyls produced by the exposure of ambient water vapor within the polygon shaped housing of hydroxyl generator 601, with the UV optics 612 and 613 irradiating light that causes the —OH radicals to form. During maintenance, the optics are completely turned off, so that no UV light will emanate out of the polygonal shaped hydroxyl generator 601.

FIG. 7 also shows the alternate embodiment for clamshell-shaped hydroxyl generator 601a, similar to hydroxyl generator 100 of FIG. 4, for a four optic version, where polygon hydroxyl generator enclosure 601a, having top wall 602, side walls 607, 608, 609, 610 of an upper shell, as well as lower walls 605, 611a, 611b of the clamshell housing of hydroxyl generator 601a. Hydroxyl generator 601 has an interior 604 in which the hydroxyl radical are formed therein. FIG. 7 also shows the electronics control box 620. The respective pairs of optics 612, 612a and 613, 613a, are supported within respective pairs of fasteners, such as C-shaped spring clasps 612a and 613a, which are each respectively mounted on bracket brace 614, which are mounted parallel lengthwise to each other inside the clamshell hexagon housing 601a. Clamshell housing 601a is openable via a hinge located near fastener 616a, which, with opposite bracket fastener 616, hold the top half of the clamshell housing to the bottom half of clamshell housing at bracket 614a.

The hydroxyl generators 601 or 601a shown in the multi-story building 600 of FIG. 8, provide clean air in the duct 650 in connection with the heating, ventilation air conditioning (HVAC) unit through which breathable air with water vapor flows, where the water vapor molecules generate the hydroxyl radicals for cleaning heated, ambient, or cooled air with the building 600.

The radical hydroxyl generators 601, 601a installed in building ducts 650 of buildings 600 of FIGS. 6, 6A, 6B, 7 and 8, are capable of destroying 99.99% (4-Log) of biological contaminants (bacterial, fungal, and viral), ensuring a clear operation of the heated, ambient, or cooled air produced by the HVAC unit 630 of building 600 shown in FIG. 8. The radical hydroxyl generating system provides all the benefits of mother-nature's natural air purification in the atmosphere, but now located in the indoor environments, such as in building 600 that people live in.

For installation of hydroxyl generator 601 or 601a into a building duct 650, the installer must first ensure that there is adequate clearance for service. If a humidifier is present, the hydroxyl generator 601 should be installed in the airstream before the humidifier Furthermore, any plastic components should be shielded from direct UV exposure.

The installer must turn off all power to the HVAC unit 630 in the building duct 650, before installation or maintenance procedures.

Wi-Fi Configuration

Additionally, once the hydroxyl generator 601 or 601a is ready for installation, it must be set up with a Wi-Fi system 28 communicating with the control box 20 of FIGS. 5, 5A and 5B.

As shown in FIG. 8, after properly installing the hydroxyl generator 601 or 601a into a wall 651 of the building duct 650 for the HVAC unit 630, it is plugged into a wall outlet and powered on, such as, for example by using a pushbutton (for example colored red) on a front panel. With the push-button pressed and the unit plugged in, the red pushbutton should illuminate. If the red pushbutton does not illuminate, it must be checked to ascertain if the unit is plugged in.

To set up the Wi-Fi network, as shown in drawing FIGS. 9, 10, 11 and 12 once the hydroxyl generator 601 or 601a is powered on and not connected to a local Wi-Fi network, a Wi-Fi hotspot will automatically be generated. To connect the hydroxyl generator 601 or 601a to a local Wi-Fi network, the installer goes to the Wi-Fi settings on any smartphone or computer. In the list of available networks, there will be a hotspot network with a name that starts with an identifier, such as, for example, "HVAC Unit #xx". Using a password, such as for example "utsisgreat", the hydroxyl generator 601 or 601a is connected to the Wi-Fi network Upon connecting to the network, a Wi-Fi Manager portal with instructions (see FIG. 9) will automatically open.

Figures 9, 10:
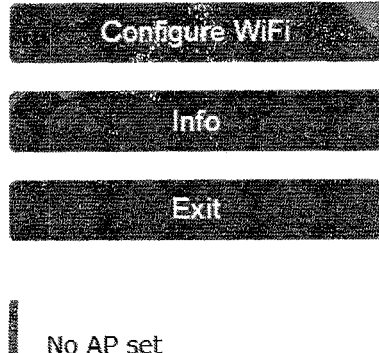
FIG. 9 is a flow chart of a Wi-Fi network manager portal communicating with operation of the radical hydroxyl generator of FIGS. 6, 6A and 6B.
FIG. 10 is a computer screen shot image of scanned Wi-Fi networks of FIG. 9, and their associated signal strength.

In the Wi-Fi Manager there will be three options: "Configure WI-FI", "Info" and "Exit". To continue setting up the unit to a local Wi-Fi network, the installer presses the instruction "Configure Wi-Fi". This will open the portal page such in the screen shot image of FIG. 10 This page of FIG. 10 shows all the scanned networks and their associated signal strength. The installer then enters the credentials of a local Wi-Fi network into the two text input boxes at the bottom of the digital screen page: labeled as "SSID" and "Password." After inserting the Wi-Fi credentials, the installer clicks the "SAVE" button shown i8n the screenshot image of FIG. 10, to finish the configuration and close the Wi-Fi Manager portal. If the input credentials are correct, the hydroxyl generator 601 or 601a will connect to the network and will turn off its hotspot. It is noted that the aforementioned Wi-Fi setup is only required during initial installation or after Wi-Fi credential change.

An indicator light, preferably yellow, is provided on the front panel of each hydroxyl generator 601 or 601a. During normal operation, this light should be off. A blinking light indicates a problem with the hydroxyl generating optics A solid light would indicate that the unit is not connected to Wi-Fi. Network 28 of FIGS. 5, 5A and 5B.

FIG. 11 a screenshot that is used to remotely check the status of the hydroxyl generator 601 or 601a in question. In the top right corner of the page the user clicks on the "Select Device" dropdown menu of FIG. 10 and select the name of the hydroxyl generator 601 or 601a being tested.

This will open a page similar to the one shown in FIG. 11. This page would be populated with real-time data sent by the selected hydroxyl generator 601 or 601a with the following data displayed on the page:

Device Name:

Power Status: Green—ON; Red—Error; White—OFF

Diagnostic LED: White—No Errors; Blinking Red—Problem with Hydroxyl Bulb(s)

Runtime: Time the bulbs have been ON for. This value can be reset.

Airflow Speed: Speed of air going through unit

Figure 12:
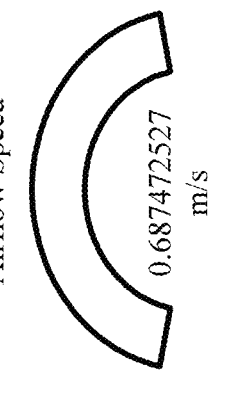
FIG. 12 is a computer screen shot image of the operation of the Wi-Fi network of the radical hydroxyl generator of FIGS. 6, 6A and 6B.

FIG. 12 is a computer screen shot image of the operation of the Wi-Fi network of the radical hydroxyl generator of FIGS. 6, 7 and 8, being installed in a building duct wall 651 or building duct 650. FIG. 12 also displays power status, diagnostics LED, hydroxyl generation status, run times, reset run times, air flow speed and an option to remove the device.

The following shows possible solutions for the problems the user may encounter during the operation of the hydroxyl radical generator in building ducts.

1—Product is not turning on: Check power source and if the voltage is adequate verify if lamps connectors are attached to the lamps. Note, this last step will require device removal.

2—Product cannot connect to the app: Check your internet connection, check if you are using the latest version of the app. Install the latest version, if needed.

3—Constant replacement of lamps due to malfunctioning: Check your air system for debris. If a humidifier is present, install the device in the air stream before it. Search for defects before installing the lamps. Contact lamp supplier for more troubleshooting or further actions.

4—Smells during operation: Check for possible contact of UV light with plastic materials inside the chamber or its vicinity.

Building Duct Device Installation

As shown in FIGS. 13-18A, in order to install the hydroxyl generator 601 or 601a in a duct 650 of a building 600 with an HVAC unit 630,s, a rectangular opening must be cut to provide access to the hydroxyl generator 601's or 601s's operative chamber, namely its clamshell housing 603 with light producing optics 612, 613 arranged therein, (or to optics 612, 612a, 613, 613a of a four bulb configuration).

A duct opening cut out 652 is made within a duct wall 651 of the building duct 650 associated with the HVAC unit 630 of building 600. A first determination must be made to ensure that there is enough cross sectional volume to accommodate the clamshell housing 603 of the hydroxyl generator and its connected structural bracket 619, to fit within the building duct 650, to allow for constant air flow within the duct 650 frontal operation of the HVAC unit 630 connected to building duct 650 of building 600.

FIG. 13 is a cross sectional top plan view from above of the duct 650, having a wall 651 into which the hydroxyl generator 601 or 601a is inserted through a cutout 652 of the duct wall 651 of duct 650. FIG. 13A is a side view of the clamshell housing 603 of hydroxyl generator 601 or 601a installed within a building duct but showing a minimal installation depth of 12 inches into the building duct 650 of building 600.

The control box 620 of the hydroxyl generator 601 or 601a is maintained outside of the duct 650 by a front structural wall 640 that is larger than the cutout 652 of wall

651 of building duct 650 provided for insertion of the polygonal clamshell housing 603 of hydroxyl generator 601 or 601a. Fastener holes are provided within front structural wall 640 of hydroxyl generator 601 or 601a, for insertion of fasteners such as threaded bolts with reciprocating rotatable nuts, to attach front structural wall 640 of hydroxyl generator 601 or 601a to the wall 651 of building duct 650. Wall 651 of building duct 650 includes the cutout insertion hole 652 for insertion of the clamshell housing 603 therein. A structural brace 619, also located within the confines of duct 650, separates the clamshell housing 603 from the inside of front structural wall 640 of the hydroxyl generator 601 or 601a.

The arrow "A" of FIG. 13 indicates the direction of air flow through the clamshell housing 603 of hydroxyl generator 601 or 601a. During installation of the clamshell housing 603 of hydroxyl generator 601 or 601a, the first step is to check the air flow orientation. This is important for the operation of the hydroxyl generator 601 or 601a located within the cut out 652 of the mounting duct wall 651 of building duct 650, which follows the indications in the device (see arrow "A") to match the hydroxyl generator 601 or 601a's orientation to the duct line air flow of building duct 650.

FIG. 14 is a front elevation view of the hydroxyl generator 601 or 601a of FIGS. 8, 13 and 13A, showing a rectangular cut out 652 in a wall 651 of the building HVAC unit duct 650, showing a vertical height of the duct opening and a lengthwise width of the duct opening, wherein the arrow "A" indicates the direction of air flow with water vapor through the radical hydroxyl generator.

In a typical installation of hydroxyl generator 601 or 601a within duct wall 651 of building duct 650, the following typical dimensions required for installation:

Horizontal hole pitch: H=4.65"
Vertical hole pitch: V=3.75"
Rectangular opening for installation: 22"×5.5"

Using a cutting instrument, such as a saw (or mechanical scissors) the opening 652 is cut into the wall 651 of building duct 650, and fastener holes, such as $\frac{3}{16}$" holes, are drilled to insert the fasteners, such as screws or nuts and bolts, to fix the hydroxyl generator 601 or 602a device in position for installation.

As shown in the exploded view of FIG. 15, the hydroxyl generator 601 or 601a is placed in position so the lighting chamber with the light generating optics are completely inside the duct line and not visible from the outside of the duct 650. The user then install the fasteners, such as crews or nuts and bolts, around the external flange of the front panel 640 of hydroxyl generator 601 or 601a Although sizes may vary, FIG. 15 shows typical height of 5.5 inches and length of 22 inches of the hydroxyl generator 601 or 601a. Operation of the Hydroxyl Radical Generator in Building Ducts
Switching On/Off:

For use in switching on/off the USA, the voltage should be 115V AC operation voltage.

For use in other countries: the user must check local voltage before install and operation.

The user then presses the main switch to turn the hydroxyl generator on/off.

This installed hydroxyl generator 601 or 601a located within the building duct 650, can be operated remotely by using the app, after the Wi-Fi settings of the aforementioned FIGS. 9-12 are first configured. The user initially finds and installs the app on either the Apple or Android marketplace, then follow the steps that will guide the user through the connectivity process. For UV light optic servicing of optics 612, 613, before servicing the interior of the hydroxyl generator 601 or 601a, the user must make sure it is switched off and disconnected from power source, to avoid injuries to the eyes of the user if exposed to intense lighting from optics 612, 613, (or to optics 612, 612a, 613, 613a of a four bulb configuration) or to exposure of the user to live electric current.

Usually, the optics 612, 613 (or to optics 612, 612a, 613, 613a of a four bulb configuration) should be replaced after two years of operation. But this can be reduced depending on operational conditions.

To get access to the lighting chamber within the clamshell polygonal housing 603 of the hydroxyl generator 601 or 601a, the hydroxyl generator 601 or 601a must be removed from the duct line within building duct 650, by doing the reverse procedure of installation. For example, first the user must unscrew the fasteners, such as three thumb-screws at the top edge of the chamber, encompassing the clamshell housing 603, to release the hinged top portion half 610 of the structure as in FIGS. 16 and 16A from the fixed bottom portion 627, and then open the chamber of the clamshell housing 603 as shown opened up in FIG. 16A.

As shown in FIG. 16B, to replace the optics 612, 613, the user must unplug the sockets from the optics (red and yellow cables) from the terminals. The user then reconnects the cables after replacing the optics within the clamshell housing 603 of the hydroxyl generator 601 or 601a.

For routine maintenance, the user should periodically clean the optics, using a rag with alcohol to remove the dirt that may cover them. To clean aluminum parts, the user wipes the surface with a rag. It is strongly recommended that the user does not handle the optics without gloves, as a clean optic enhances the product performance.

Figures 17, 18, 18A:
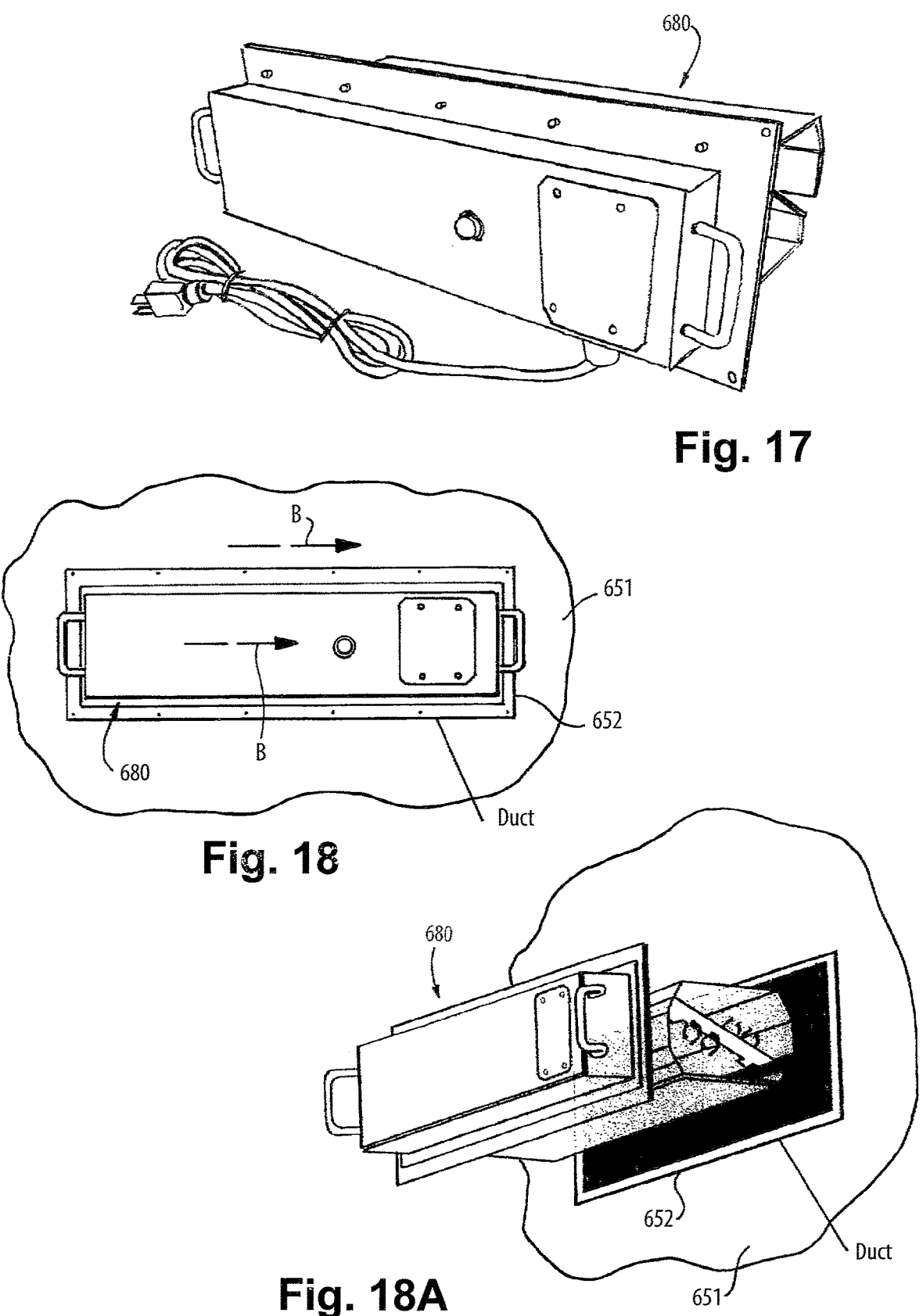
FIG. 17 is a perspective view of an in-duct retrofit HVAC hydroxyl generator installable in a duct of an HVAC unit of a building, wherein a plug and electrical wire are provided for connection to a power supply of the building shown in FIG. 8.
FIG. 18 is a front elevation view as in FIG. 17 of the retrofit hydroxyl generator installed in a duct in a building.
FIG. 18A is an exploded perspective view of a retrofit hydroxyl generator being installed in a wall of a building duct, as in FIGS. 17 and 18.

FIG. 17 shows an in-duct retrofit HVAC hydroxyl generator 680 installable in a duct of an HVAC unit of a building 600, wherein a plug and electrical wire are provided for connection to a power supply of the building 600 shown in FIG. 8.

FIG. 18 shows the front view of the retrofit hydroxyl generator 680 installed in a wall of the duct 650 in the building 600, such as building 600 of FIG. 8, where the arrows "B" reflect the air flow and the orientation of retrofit hydroxyl generator in the same direction as arrow "B".

FIG. 18A is an exploded perspective view of the retrofit hydroxyl generator 680 being installed in a wall of a building duct 650 of building 600, as in FIGS. 17 and 18.

Designed to easily install at the manifold of the HVAC duct system the present invention enables the hydroxyl radical generator 601, 601a or 680 to disperse hydroxyl radicals throughout all areas served by the air conditioning or heating system 630 of a building duct 650 of a building 600. The installation takes only minutes, plugs in or can be hard-wired for easy connection and operates simultaneously with the air handling system in a building such as a home, building offices, industrial facilities, etc.

The hydroxyl generators for building ducts of buildings 600, shown in FIGS. 6-18A will inactivate any volatile organic compounds (VOCs) or pathogens, such as virus, bacteria, or fungi, anywhere in the air of the buildings and/or having the controls of FIGS. 5, 5A, 5B and/or 5C.

CONCLUSION

The hydroxyl generator systems of the present invention are designed to neutralize and destroy virus' everywhere safely and effectively, while purifying and sanitizing breathable heated, ambient, or cooled air emanating from a source and neutralizing up to 99.9999% of tested virus, including Covid-19 virus. The present invention also helps occupants an occupied space who are afflicted with asthma and air-borne allergies, including full air and surface protection, including in crevices between other surfaces.

The hydroxyl generator systems of the present invention can be placed in any environment where pristine air is required, in a state of the art technology that is chemical free, safe for people, pets and plants.

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing the scope of the invention, as noted in the appended Claims.

What is claimed:

1. An air purification system (601) configured for retrofit with respect to an opening made in a wall of an existing air duct of a heating, ventilation, and air conditioning (HVAC) system of a building, said air purification system comprising:

a cover plate (640), said cover plate comprising:
a first side;
a second side, said second side being configured to mount against the duct;
a periphery sized to cover and extend beyond an entire periphery of the opening in the wall of the existing air duct; and
a plurality of holes, each configured to admit a mounting fastener therethrough to secure said cover plate (640) to the duct to cover the opening;

a lamp housing, said lamp housing being linearly elongated and configured to extend in an axial direction from a first end to a second end, with an opening to form an air inlet at said first end and an air outlet opening at said second end, to accommodate air flow in the duct into said air inlet and out from said air outlet, when said cover plate (640) is secured to the duct to cover the opening;

a first lamp bracket (614), said first lamp bracket comprising: a flat plate; wherein said flat plate is configured to mount to and to extend between a first side of said lamp housing and a second side of said lamp housing, in proximity to a first end of said lamp housing, and to extend parallel to the axial direction of said lamp housing;

a second lamp bracket (615), said second lamp bracket comprising: a flat plate; wherein said flat plate of said second lamp bracket is configured to mount to and to extend between a first side of said lamp housing and a second side of said lamp housing, in proximity to a second end of said lamp housing, and to extend parallel to the axial direction of said lamp housing;

a first plurality of spring clasps (612a, 612b), each mounted to said first lamp bracket;

a second plurality of spring clasps, each mounted to said second lamp bracket;

a plurality of UV bulbs (612, 613);

wherein said first plurality of spring clasps and said second plurality of spring clasps are configured to releasably support said plurality of UV bulbs in a spaced arrangement within said lamp housing, with each being oriented parallel to the axial direction of said lamp housing;

wherein each of said plurality of UV bulb are configured to emit ultraviolet light to generate hydroxyl radicals from water vapor contained within the air flow in the duct, the hydroxyl radicals being usable to deactivate volatile organic chemicals (VOCs), viruses, bacteria, mold, and pathogens in the air flow in the duct;

a control box (620), said control box comprising:
a box housing; and
a microprocessor and electronics configured to communicate with, and control operation of, each of said plurality of UV bulbs;

a mounting bracket (619);

wherein said mounting bracket (619) is configured to mount said lamp housing to said cover plate (640); and wherein said mounting bracket (619) is configured to support said lamp housing at a substantially central position within the duct, with each of said UV bulbs oriented parallel to a direction of air flow in the duct, when said cover plate (640) is secured to the duct to cover the opening.

2. The air purification system (601) according to claim 1, wherein said first lamp housing portion and said second lamp housing portion form an octagonal cross-sectional shape when said second lamp portion is pivoted into the closed position.

3. The air purification system (601) according to claim 2, wherein said box housing is secured to said first side of said mounting plate to position said control box (620) outside of the duct, when said cover plate (640) is secured to the duct to cover the opening in the duct.

4. The air purification system (601) according to claim 3, wherein said lamp housing comprises:
a first lamp housing portion;
a second lamp housing portion;
a hinge;
wherein said hinge in configured to pivotally mount said second lamp housing portion to said first lamp housing portion to pivot between a closed position and an open position;

wherein said first lamp bracket (614) is mounted to extend from a first side of said first housing portion to a second side of said first housing portion, in proximity to a first end of said first housing portion; and wherein said second lamp bracket (615) is mounted to extend from said first side of said first housing portion to said second side of said first housing portion, in proximity to a second end of said first housing portion.

5. The air purification system (601) according to claim 4, wherein said spaced arrangement comprises: said first plurality of spring clasps and said second plurality of spring clasps being positioned to mount said plurality of UV bulbs in a symmetric arrangement within said octagonal cross-sectional shape.

6. The air purification system (601) according to claim 5, wherein said spaced arrangement comprises: said first plurality of spring clasps and said second plurality of spring clasps being positioned to mount said plurality of UV bulbs in a staggered arrangement within said octagonal cross-sectional shape.

7. The air purification system (601) according to claim 6, wherein said mounting bracket (619) comprises:
an elongated first flange;
an elongated second flange;
an elongated third flange;

wherein said elongated second flange and said elongated third flange each extend perpendicularly away from respective distal ends of said elongated first flange to thereby form a channel-shaped cross-sectional portion;

an elongated fourth flange configured to extend away from a distal end of said elongated second flange;

an elongated fifth flange configured to extend away from a distal end of the third flange;

an elongated sixth flange configured to extend away from a distal end of said elongated fifth flange;

wherein said elongated fourth flange and said elongated fifth flange are configured to mount against and support a first angled side and a second angled side of said octagonal cross-sectional shape;

wherein said elongated sixth flange is configured to support a bottom surface of said octagonal cross-sectional shape; and wherein each of said elongated first flange, said elongated second flange, and said elongated third flange, said elongated fourth flange, said elongated fifth flange, and said elongated sixth flange are elongated parallel to the axial direction of said lamp housing.

8. The air purification system (601) according to claim 7, comprising: a first handle and a second handle, said first handle and said second handle configured to extend away from a first end and a second end of said box housing, respectively.

9. The air purification system (601) according to claim 8, further comprising:

a UV light sensor, said UV light sensor configured to detect emission of UV light from said plurality of UV bulbs, and to provide feedback to indicate a need for bulb replacement; and a fire sensor configured to detect excess heat in said system.

10. The air purification system (601) according to claim 9, wherein said microprocessor and electronics are configured to wirelessly communicate with a smartphone to remotely monitor and control operation of said system.

11. The air purification system (601) according to claim 10, further comprising: a plurality of indicator lights configured to indicate a status of said system, including power status, diagnostic information, runtime of the UV bulbs emitting UV light, and airflow speed.

* * * * *